(12) United States Patent
Laikhter et al.

(10) Patent No.: US 8,030,460 B2
(45) Date of Patent: *Oct. 4, 2011

(54) COMPOUNDS AND METHODS FOR LABELING OLIGONUCLEOTIDES

(75) Inventors: Andrei Laikhter, Iowa City, IA (US); Joseph A. Walder, Chicago, IL (US); Mark Behlke, Coralville, IA (US); Mikhail Podyminogin, Coralville, IA (US); Yawfui Yong, Coralville, IA (US)

(73) Assignee: Integrated DNA Technologies, Inc., Skokie, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/853,741

(22) Filed: Aug. 10, 2010

(65) Prior Publication Data

US 2010/0298554 A1 Nov. 25, 2010

Related U.S. Application Data

(62) Division of application No. 12/623,811, filed on Nov. 23, 2009, now Pat. No. 7,803,936, which is a division of application No. 12/535,220, filed on Aug. 4, 2009, now Pat. No. 7,645,872, which is a division of application No. 12/352,125, filed on Jan. 12, 2009, now Pat. No. 7,605,243, which is a division of application No. 11/438,606, filed on May 22, 2006, now Pat. No. 7,476,735.

(60) Provisional application No. 60/683,278, filed on May 20, 2005.

(51) Int. Cl.
*C07C 245/00* (2006.01)
*C12Q 1/68* (2006.01)
*C07H 21/00* (2006.01)
*C07H 21/02* (2006.01)
*C07K 16/00* (2006.01)

(52) U.S. Cl. ... 534/558; 536/23.1; 536/24.2; 536/25.32; 536/26.6; 435/6; 530/391.3

(58) Field of Classification Search ..... 435/6; 536/23.1, 536/24.2, 25.32, 26.6; 534/558; 530/391.3
See application file for complete search history.

(56) References Cited

U.S. PATENT DOCUMENTS
2,264,303 A   12/1941   Dickey
(Continued)

FOREIGN PATENT DOCUMENTS
DE   2546535   4/1977
(Continued)

OTHER PUBLICATIONS
7th International Symposium, held 2001, pp. 1-14, 7th International Symposium & Exhibition Solid Phase Synthesis & Combinatorial Chemical Libraries, Sep. 18-22, 2001—University of Southampton, England, UK.
(Continued)

*Primary Examiner* — Jezia Riley
(74) *Attorney, Agent, or Firm* — Michael Best & Friedrich LLP

(57) ABSTRACT

A compound having the general formula shown below:

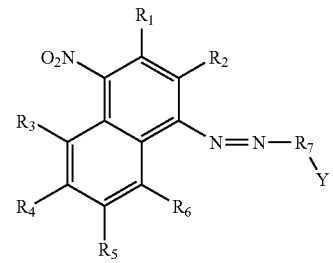

where $R_{1-6}$ are independently selected from the group consisting of an electron withdrawing group, an alkyl group, an aryl group, hydrogen, a heteroaryl group, and a five or six member ring structure formed from the $R_1$ and $R_2$ pair, the $R_3$ and $R_4$ pair, the $R_4$ and $R_5$ pair, or the $R_5$ and $R_6$ pair; $R_7$ is a substituted or unsubstituted aryl group; and Y is a nucleophile.

25 Claims, 15 Drawing Sheets

Scheme 1

U.S. PATENT DOCUMENTS

| | | | |
|---|---|---|---|
| 3,218,309 | A | 11/1965 | Elslager et al. |
| 3,407,189 | A | 10/1968 | Merian |
| 3,970,617 | A | 7/1976 | Bruno |
| 4,358,535 | A | 11/1982 | Falkow et al. |
| 4,439,356 | A | 3/1984 | Khanna et al. |
| 4,683,194 | A | 7/1987 | Saiki et al. |
| 4,683,195 | A | 7/1987 | Mullis et al. |
| 4,683,202 | A | 7/1987 | Mullis |
| 4,711,955 | A | 12/1987 | Ward et al. |
| 4,820,630 | A | 4/1989 | Taub |
| 4,868,103 | A | 9/1989 | Stavrianopoulos et al. |
| 4,868,105 | A | 9/1989 | Urdea et al. |
| 4,889,818 | A | 12/1989 | Gelfand et al. |
| 4,914,210 | A | 4/1990 | Levenson et al. |
| 4,954,630 | A | 9/1990 | Klein et al. |
| 4,996,143 | A | 2/1991 | Heller et al. |
| 5,011,769 | A | 4/1991 | Duck et al. |
| 5,108,892 | A | 4/1992 | Burke et al. |
| 5,124,246 | A | 6/1992 | Urdea et al. |
| 5,188,934 | A | 2/1993 | Menchen et al. |
| 5,210,015 | A | 5/1993 | Gelfand et al. |
| 5,214,136 | A | 5/1993 | Lin et al. |
| 5,272,259 | A | 12/1993 | Claussen et al. |
| 5,304,645 | A | 4/1994 | Klein et al. |
| 5,312,728 | A | 5/1994 | Lizardi et al. |
| 5,326,679 | A | 7/1994 | Yanagisawa et al. |
| 5,328,824 | A | 7/1994 | Ward et al. |
| 5,451,463 | A | 9/1995 | Nelson et al. |
| 5,455,157 | A | 10/1995 | Hinzpeter et al. |
| 5,487,972 | A | 1/1996 | Gelfand et al. |
| 5,492,806 | A | 2/1996 | Drmanac et al. |
| 5,502,177 | A | 3/1996 | Matteucci et al. |
| 5,512,667 | A | 4/1996 | Reed et al. |
| 5,514,785 | A | 5/1996 | Van Ness et al. |
| 5,525,464 | A | 6/1996 | Drmanac et al. |
| 5,556,752 | A | 9/1996 | Lockhart et al. |
| 5,696,251 | A | 12/1997 | Arnold, Jr. et al. |
| 5,801,155 | A | 9/1998 | Kutyavin et al. |
| 5,804,375 | A | 9/1998 | Gelfand et al. |
| 5,824,796 | A | 10/1998 | Petrie et al. |
| 5,830,653 | A | 11/1998 | Froehler et al. |
| 5,846,726 | A | 12/1998 | Nadeau et al. |
| 5,849,482 | A | 12/1998 | Meyer, Jr. et al. |
| 5,876,930 | A | 3/1999 | Livak et al. |
| 5,942,610 | A | 8/1999 | Nelson et al. |
| 5,952,202 | A | 9/1999 | Aoyagi et al. |
| 6,007,992 | A | 12/1999 | Lin et al. |
| 6,028,183 | A | 2/2000 | Lin et al. |
| 6,114,518 | A | 9/2000 | Pitner et al. |
| 6,117,973 | A | 9/2000 | Batz et al. |
| 6,117,986 | A | 9/2000 | Nardone et al. |
| 6,214,979 | B1 | 4/2001 | Gelfand et al. |
| 6,312,894 | B1 | 11/2001 | Hedgpeth et al. |
| 6,316,610 | B2 | 11/2001 | Lee et al. |
| 6,323,337 | B1 | 11/2001 | Singer et al. |
| 6,399,392 | B1 | 6/2002 | Haugland et al. |
| 6,416,953 | B1 | 7/2002 | Heller |
| 6,441,159 | B1 | 8/2002 | Lukhtanov et al. |
| 6,448,407 | B1 | 9/2002 | Lee et al. |
| 6,451,535 | B1 | 9/2002 | Jenne et al. |
| 6,465,175 | B2 | 10/2002 | Horn et al. |
| 6,465,644 | B1 | 10/2002 | Yan et al. |
| 6,485,901 | B1 | 11/2002 | Gildea et al. |
| 6,531,581 | B1 | 3/2003 | Nardone et al. |
| 6,531,589 | B1 | 3/2003 | Iyer et al. |
| 6,531,591 | B1 | 3/2003 | Fensholdt |
| 6,653,473 | B2 | 11/2003 | Reed et al. |
| 6,699,975 | B2 | 3/2004 | Reed et al. |
| 6,727,356 | B1 | 4/2004 | Reed et al. |
| 6,790,945 | B2 | 9/2004 | Lukhtanov et al. |
| 6,800,728 | B2 | 10/2004 | Schwartz |
| 6,825,331 | B2 | 11/2004 | Manoharan et al. |
| 6,875,858 | B1 | 4/2005 | DeFrancq et al. |
| 7,122,383 | B2 | 10/2006 | Jones et al. |
| 7,173,125 | B2 | 2/2007 | Schwartz et al. |
| 7,439,341 | B2 | 10/2008 | Laikhter et al. |
| 7,476,735 | B2 | 1/2009 | Laikhter et al. |
| 7,605,243 | B2 | 10/2009 | Laikhter et al. |
| 7,645,872 | B2 | 1/2010 | Laikhter et al. |
| 2002/0034754 | A1 | 3/2002 | Reed et al. |
| 2002/0137070 | A1 | 9/2002 | Mirkin et al. |
| 2003/0082547 | A1 | 5/2003 | Ewing et al. |
| 2003/0096254 | A1 | 5/2003 | Reed et al. |
| 2003/0144499 | A1 | 7/2003 | McGall et al. |
| 2004/0110308 | A1 | 6/2004 | Laikhter et al. |
| 2004/0180343 | A1 | 9/2004 | Weber |
| 2007/0218490 | A1 | 9/2007 | Laikhter et al. |
| 2009/0053821 | A1 | 2/2009 | Laikhter et al. |
| 2010/0076181 | A1 | 3/2010 | Laikhter et al. |

FOREIGN PATENT DOCUMENTS

| | | |
|---|---|---|
| EP | 0070685 | 1/1983 |
| EP | 0070686 | 1/1983 |
| EP | 0070687 | 1/1983 |
| EP | 0152886 | 8/1985 |
| EP | 0185494 | 6/1986 |
| EP | 0246864 | 11/1987 |
| EP | 0272007 | 6/1988 |
| EP | 0320308 | 6/1989 |
| EP | 0357011 | 3/1990 |
| EP | 0439182 | 7/1991 |
| GB | 1394368 | 5/1975 |
| GB | 1533121 | 11/1978 |
| JP | 52-88681 | 7/1977 |
| JP | 52-91031 | 8/1977 |
| WO | WO 89/09284 | 10/1989 |
| WO | WO 89/10979 | 11/1989 |
| WO | WO 90/14353 | 11/1990 |
| WO | WO 91/05060 | 4/1991 |
| WO | WO 92/10588 | 6/1992 |
| WO | WO 96/17957 | 6/1996 |
| WO | WO 96/28460 | 9/1996 |
| WO | WO 96/34983 | 11/1996 |
| WO | 96/40662 | 12/1996 |
| WO | WO 97/29154 | 8/1997 |
| WO | WO 97/39008 | 10/1997 |
| WO | WO 99/14226 | 3/1999 |
| WO | WO 99/37717 | 7/1999 |
| WO | WO 99/40226 | 8/1999 |
| WO | WO 99/51621 | 10/1999 |
| WO | WO 99/51775 | 10/1999 |
| WO | WO 99/64431 | 12/1999 |
| WO | WO 00/06771 | 2/2000 |
| WO | WO 00/70685 | 11/2000 |
| WO | WO 01/04129 | 1/2001 |
| WO | WO 01/42505 | 6/2001 |
| WO | WO 01/86001 | 11/2001 |
| WO | WO 2004/026804 | 4/2004 |
| WO | WO 2004/113562 | 12/2004 |
| WO | WO 2005/049849 | 6/2005 |
| WO | WO 2006/127507 | 4/2007 |

OTHER PUBLICATIONS

Conference Proceedings, retrieved 2010, two pages, Innovation and Perspectives in Solid Phase Synthesis & Combinatorial Libraries: Peptides, Proteins and Nucleic Acids—Small Molecule Organic Chemistry Diversity, Collected Papers, International Symposium, 7th, Southampton, United Kingdom, Sep. 18-22, 2001, Roger Epton, Editor.

Easy Q&Q PCR, www.eurogentec.be/code/en/product_easy_qq.htm, visited May 9, 2002, 4 pages.

Encyclopedia Britannica (2008) "Nucleic Acid," Encyclopedia Britannica Online (Jul. 11, 2008) www.search.eb.com/eb/article-256731.

Genbank Accession No. AF298116, Rose et al., "Mus musculus bHLH protein Ptfl-p48 gene," (2001) 6 pages.

Gibson, V. et al., "Molecular modelling of anthraquinone-oligodeoxynucleotide conjugates," Pharm. Sci. (1996) 2:545-548.

Gorelick, M.V. et al., "Effect of benzannelation on the coloration of p-aminoazo compounds," Zhurnal Organicheskoi Khimii (1980) 16(9):1927-1933—Abstract only—Accession No. 1981:193676.

Greene, T.W. and Wuts, P.G.M., *Protective Groups in Organic Synthesis*, (1999) 3rd Ed. John Wiley & Sons, Inc., U.S. (Book Not Provided).

Ho, M.S. et al., "Azo polymers for reversible optical storage. 7. The effect of the size of the photochromic groups," Macromolecules (1995) 28(18):6124-6127 (Abstract only—Accession No. 1995:746851).

Hugentobler, M. et al., "Compounds with a metal-arene σ-bond. Part 2. Cyclometalation of arylazo compounds. Part 2. Regioselectivity of the cyclopalladation of some substituted 1-arylazonaphthalenes," Helvetica Chimica Acta (1982) 65(4):1202-1211 (Abstract only—Accession No. 1982:616430).

Jenkins, J.H., Senior Librarian at the United States Patent and Trademark Office, email dated Mar. 18, 2010 and previously related email corespondence, pp. 1-2.

Ju, J. et al., "Fluorescence energy transfer dye-labeled primers for DNA sequencing and analysis," Proc. Natl. Acad. Sci. USA (1995) 92:4347-4351.

Kerzhner, B.K. et al., "Photoisomerization of aromatic azo compounds adsorbed on a hydroxylated surface," Zhurnal Obshchei Khimii (1983) 53(10):2303-2306 (Abstract only—Accession No. 1984:50840).

May, J.P. et al., "A new dark quencher for use in genetic analysis," Chem. Commun. (2003) 970-971.

May, J.P. et al., "A novel dark quencher for oligonucleotide probes: synthesis and applications," poster presentation from TIDES 2002 IBC Oligonucleotide and Peptide Technology Conference, May 6-8, 2002, Las Vegas, Nevada (2 pages).

May, J.P. et al., "Synthesis of a novel dark quencher for use with long wavelength dyes in oligonucleotide probes," Innovation and Perspectives in Solid Phase Synthesis & Combinatorial Libraries: Peptides, Proteins and Nucleic Acids Small Molecule Organic Chemical Diversity, Collected Papers, 7th International Symposium, Southampton, United Kingdom, Sep. 18-22, 2002, 231-233.

Miyashita, T. et al., "Novel dinucleoside phosphotriester unit conjugated with an intercalative moiety in a stereospecific manner enhances thermal stability of an alternate-stranded triple helix," Tetrahedron Letters (2003) 44:7399-7402.

Mori, K. et al., "Oligodeoxynucleotide analogs with 5'-linked anthraquinone," FEBS Letters (1989) 249(2):213-218.

Morier-Teissier, E. et al., "Free radical production and DNA cleavage by copper chelating peptide-anthraquinones," Anti-Cancer Drug Design (1990) 5:291-305.

Mullis, K. et al., "Specific Enzymatic Amplification of DNA In Vitro: The Polymerase Chain Reaction," Cold Spring Harbor Symp. Quant. Biol. (1986) 51:263-273.

PR Newswire, Announcing IBC's Tides 2002: Oligonucleotide and Peptide Technology Conferences May 6-8, 2002, Las Vegas, NV, Copyright 2002, PR Newswire Association LLC, pp. 1-2, website (retrieved Mar. 18, 2010): thefreelibrary.com/_/print/PrintArticle.aspx?id=82059345.

Puskas, L.G. et al., "Diamino-Antraquinone: A New Intercalating Agent. Synthesis and Linking to Oligodeoxynucleotide," *Nucleosides & Nucleotides* (1995) 14(3-5):967-968.

Rose, S.D. et al., "The Role of PTF1-P48 in pancreatic acinar gene expression," *J. Biol. Chem.* (2001) 276(47):44018-44026.

Schuster, G.B., "Long-range charge transfer in DNA: transient structural distortions control the distance dependence," Acc. Chem. Res. (2000) 33:253-260.

Zielske, A.G., "(Tosyloxy)anthraquinones: Versatile Synthons for the Preparation of Various Aminoanthraquinones," *J. Org. Chem.* (1987) 52:1305-1309.

European Patent Office Action for Application No. 06770717.4 dated Jun. 8, 2010 (3 pages).

International Preliminary Report on Patentability for Application No. PCT/US04/37932 dated Nov. 16, 2006 (8 pages).

International Search Report and Written Opinion for Application No. PCT/US04/37932 dated Jul. 28, 2006 (10 pages).

International Preliminary Report on Patentability for Application No. PCT/US03/029324 dated May 28, 2004 (4 pages).

International Search Report for Application No. PCT/US03/029324 dated Feb. 6, 2004 (1 page).

United States Office Action for U.S. Appl. No. 10/987,608 dated Mar. 28, 2008 (8 pages).

United States Office Action for U.S. Appl. No. 10/987,608 dated Oct. 5, 2007 (7 pages).

United States Office Action for U.S. Appl. No. 12/252,721 dated Apr. 30, 2010 (10 pages).

United States Office Action for U.S. Appl. No. 10/666,998 dated Jan. 8, 2008 (14 pages).

United States Office Action for U.S. Appl. No. 10/666,998 dated Jul. 16, 2008 (9 pages).

United States Office Action for U.S. Appl. No. 10/666,998 dated Jan. 16, 2009 (18 pages).

United States Office Action for U.S. Appl. No. 10/666,998 dated Sep. 17, 2009 (10 pages).

United States Patent Notice of Allowance for U.S. Appl. No. 10/666,998 dated Jan. 25, 2010 (12 pages).

United States Patent Office Action for U.S. Appl. No. 10/666,998 dated Jul. 1, 2010 (8 pages).

Agrawal, S. et al., "Efficient methods for attaching non-radioactive labels to the 5' ends of synthetic oligodeoxyribonucleotides," Nuc. Acids Res. (1986) 14:6227-6245.

Austermann, S. et al., "Inhibition of human immunodeficiency virus type 1 reverse transcriptase by 3'-blocked oligonucleotide primers," Biochem. Pharm. (1992) 43(12):2581-2589.

Bollum, F.J., "Oligodeoxyribonucleotide-primed reactions catalyzed by calf thymus polymerase," J. Bio. Chem. (1962) 237(6):1945-1949.

Cardullo, R.A et al., "Detection of nucleic acid hybridization by nonradiative fluorescence resonance energy transfer," Proc. Natl. Acad. Sci. USA (1988) 85:8790-8794.

Dey, S. and Sheppard, T.L., "Ketone-DNA: a versatile postsynthetic DNA decoration platform," Org. Lett. (2001) 3(25):3983-3986.

Gelfand, D.H., "Taq DNA Polymerase," PCR Technology Principles and Applications for DNA Amplification, Stockton Press, NY, Ehrlich ed. (1989) Ch. 2, 17-22.

Haugland, R.P. et al., *Handbook of Flourescent Probes and Research Chemicals*, (1992) 5th Ed. Molecular Probes, Inc., Oregon, U.S. (Book Not Provided).

Heesemann, J., "Studies on monolayers. 1. Surface tension and absorption spectroscopic measurements of monolayers of surface-active azo and stilbene dyes," J. Am. Chem. Soc. (1980) 102(7):2167-2176.

Heller, M.J. et al., "Chemiluminescent and fluorescent probes for DNA hybridization systems," Rapid Detection and Identification of Infectious Agents (1985) Academic Press, Inc., Orlando, Kingsbury et al. eds. 245-256.

Iyer, R.P. et al., "3H-1,2-benzodithiole-3-one 1,1-dioxide as an improved sulfurizing reagent in the solid-phase synthesis of oligodeoxyribonucleoside phosphorothioates," J. Am. Chem. Soc. (1990) 112:1253-1254.

Lawyer, F.C. et al., "Isolation, characterization, and expression in *escherichia coli* of the DNA polymerase gene from thermus aquaticus," J. Biol. Chem. (1989) 264(11):6427-6437.

Lehman, I.R. et al., "Persistence of deoxyribonucleic acid polymerase I and its 5' →3' exonuclease activity in PolA mutants of *escherichia coli* K12," J. Biol. Chem. (1973) 248(22):7717-7723.

Marshall, "Rules for the visible absorption spectra of halogenated fluorescein dyes," Histochemical J. (1975) 7:299-303.

Matthews, J.A. et al., "Analytical strategies for the use of DNA probes," Analy. Biochem. (1988) 169:1-25.

Misiura, K. et al., "Biotinyl and phosphotyrosinyl phosphoramidite derivatives useful in the incorporation of multiple reporter groups on synthetic oligonucleotides," Nucleic Acids Research (1990) 18(15):4345-4354.

Morrison, L.E. et al., "Solution-phase detection of polynucleotides using interacting fluorescent labels and competitive hybridization," Anal. Biochem. (1989) 183:231-244.

Noble, S.A. et al, "Methylphosphonates as probes of protein-nucleic acid interactions," Nuc. Acids Res. (1984) 12(7):3387-3404.

Proudnikov, D. et al., "Chemical methods of DNA and RNA fluorescent labeling," Nucleic Acids Res. (1996) 24(22):4535-4542.

Setlow, P. et al., "Deoxyribonucleic acid polymerase: two distinct enzymes in one polypeptide," J. Biol. Chem. (1972) 247(1):224-231.

Sum, D.T.H.M. et al., "Aqueous solubility, octanol solubility, and octanol/water partition coefficient of nine hydrophobic dyes," Envir. Toxic. Chem. (1999) 18(6):1109-1117.

Telser, J. et al., "Synthesis and characterization of DNA oligomers and duplexes containing covalently attached molecular labels: comparison of biotin, fluorescein, and pyrene labels by thermodynamic and optical spectroscopic measurements," J. Am. Chem. Soc. (1989) 111:6966-6967.

Tu, C-P.D. et al., "3'-end labeling of DNA with [α-32P]cordycepin-5'-triphosphate," Gene (1980) 10:177-183.

International Search Report and Written Opinion for Application No. PCT/US06/19552 dated Dec. 27, 2006 (9 pages).

United States Patent Office Action for U.S. Appl. No. 12/623,811 dated Feb. 17, 2010 (5 pages).

Boturyn, D. et al., "Synthesis of fluorescent probes for the detection of abasic sites in DNA," Tetrahedron (1997) 53 (15):5485-5492.

Ito, T. et al., "Reductive electron injection into duplex DNA by aromatic amines," J. Am. Chem. Soc. (2004) 126:15552-15559.

Australian Patent Office Action for Application No. 2006251637 dated Feb. 22, 2011 (3 pages).

European Patent Office Action for Application No. 06770717.4 dated Mar. 11, 2011 (11 pages).

United States Patent Office Action for U.S. Appl. No. 12/252,721 dated Oct. 15, 2010 (9 pages).

United States Patent Office Action for U.S. Appl. No. 12/252,721 dated Apr. 20, 2011 (7 pages).

Kuball, H-G. et al., "Helical twisting power of chiral mono- and bis-aminoanthraquinones," J. Mater. Chem. (1995) 5 (12):2167-2174.

United States Patent Office Action for U.S. Appl. No. 12/853,755 dated Jul. 1, 2011 (20 pages).

US 6,255,052, 05/2001, Batz et al. (withdrawn)

Scheme 1

Scheme 4

Where R = Biotin, peptide, DNA, etc.

FAM-CCAGCGACCCTGATTATGGCCTCCCT-IBAOket    SEQ ID NO: 1

FAM-CCAGCGACCCTGATTATGGCCTCCCT-IBAOket       SEQ ID NO: 1

FAM-CCAGCGACCCTGATTATGGCCTCCCT-IBAOdU        SEQ ID NO: 2

FAM-CCAGCGACCCTGATTATGGCCTCCCT-IBAOC7    SEQ ID NO: 3

FAM-CCAGCGACCCTGATTATGGCCTCCCT-Eclipse     SEQ ID NO: 4

```
FAM-CCAGCGACCCTGATTATGGCCTCCCT-IBAOket      SEQ ID NO: 1
FAM-CCAGCGACCCTGATTATGGCCTCCCT-IBAOdU       SEQ ID NO: 2
FAM-CCAGCGACCCTGATTATGGCCTCCCT-IBAOC7       SEQ ID NO: 3
FAM-CCAGCGACCCTGATTATGGCCTCCCT-Eclipse      SEQ ID NO: 4
```

```
FAM-ATGGCGGTTCTCATGCTGGCAAC-IBAOC7              SEQ ID NO: 11
FAM-ATGGCGGT(iIBAOdU)CTCATGCTGGCAAC-C3sp        SEQ ID NO: 12
FAM-ATGGCGGTT(iIBAOdU)TCATGCTGGCAAC-C3sp        SEQ ID NO: 13
FAM-ATGGCGGTTCTC(iIBAOdU)TGCTGGCAAC-C3sp        SEQ ID NO: 14
```

COMPOUNDS AND METHODS FOR LABELING OLIGONUCLEOTIDES

CROSS REFERENCE TO RELATED APPLICATIONS

This application is a divisional of U.S. application Ser. No. 12/623,811 filed Nov. 23, 2009, which is a divisional of Ser. No. 12/535,220, filed Aug. 4, 2009, now U.S. Pat. No. 7,645,872, which is a divisional of U.S. application Ser. No. 12/352,125, filed Jan. 12, 2009, now U.S. Pat. No. 7,605,243, which is a divisional of U.S. application Ser. No. 11/438,606, filed May 22, 2006, now U.S. Pat. No. 7,476,735, which claims the priority benefit of U.S. Provisional Application No. 60/683,278, filed May 20, 2005. These applications are incorporated herein by reference in their entireties.

FIELD OF THE INVENTION

This invention pertains to compounds and methods for labeling oligonucleotides. The invention also provides kits that contain at least one of the disclosed compounds.

BACKGROUND OF THE INVENTION

Oligonucleotides are often modified or labeled with reporter moieties such as quenchers, fluorophores, biotin, etc. These labeled oligonucleotides can provide information regarding binding and other biological phenomena, the structure of DNA, the association of macromolecules, and the size and mobility of protein and DNA complexes.

Several attachment chemistries are currently used for modifying oligonucleotides. For example, primary amino groups are widely used to attach modifiers, reporter moieties or labels to an oligonucleotide. In addition, they can be used to attach an oligonucleotide to a solid surface.

Stable Schiff base linkers have been used for the synthesis of labeled oligonucleotides. (Dey & Sheppard (2001) Org. Lett. Vol. 3, 25:3983-3986, which is incorporated herein by reference). The methods have been limited to the post-synthetic attachment of labels, and the proposed methods have not been commercially viable alternatives to standard synthesis approaches. Previously described post-synthetic methods permit the incorporation of only a single type of reporter moiety or multiple copies of the same reporter moiety into an oligonucleotide.

Labeled oligonucleotides have a wide variety of useful applications. For example, light quenching processes that rely on the interaction of a fluorophore and quencher as their spatial relationship changes can be used in convenient processes for detecting and/or identifying oligonucleotides and other biological phenomena. In one such method, the change in fluorescence of a fluorophore or quencher can be monitored as two oligonucleotides (one containing a fluorophore and one containing a quencher) hybridize to each other. The hybridization can be detected without intervening purification steps that separate unhybridized from hybridized oligonucleotides. Currently, quencher groups are commonly placed at the end of a probe sequence while the fluorophore is placed at the opposite end, solely for ease of synthesis. However, in some applications, such as real-time PCR, dual-labeled probes are more effective when the labels are placed closer to each other.

Perhaps the most common mechanism of fluorescent quenching is fluorescent resonance energy transfer ("FRET"). For FRET to occur, a fluorophore and a fluorescent quencher must be within a suitable distance for the quencher to absorb energy from the donor. In addition, there must be overlap between the emission spectrum of the fluorescent donor and the absorbance spectrum of the quencher. This requirement complicates the design of probes that utilize FRET because not all potential quencher/fluorophore pairs can be used. For example, the quencher known as BHQ-1, which absorbs light in the wavelength range of about 520-550 nm, can quench the fluorescent light emitted from the fluorophore, fluorescein, which fluoresces maximally at about 520 nm. In contrast, the quencher BHQ-3, which absorbs light in the wavelength range of about 650-700 nm would be almost completely ineffective at quenching the fluorescence of fluorescein through FRET but would be quite effective at quenching the fluorescence of the fluorophore known as Cy5 which fluoresces at about 670 nm.

Oligonucleotides labeled with fluorophores and quenchers can also be used to monitor the kinetics of PCR amplification. For example, a PCR reaction is performed using oligonucleotides designed to hybridize to the 3' side ("downstream") of an amplification primer so that the 5'-3' exonuclease activity of a polymerase digests the 5' end of the probe, cleaving off one of the dyes. The fluorescence intensity of the sample increases and can be monitored as the probe is digested during the course of amplification.

Similar oligonucleotide compositions may be used in other molecular/cellular biology and diagnostic assays, such as end-point PCR, in situ hybridizations, in vivo DNA and RNA species detection, single nucleotide polymorphism (SNPs) analysis, enzyme assays, and in vivo and in vitro whole cell assays.

BRIEF SUMMARY OF THE INVENTION

The invention provides a method for linking a reporter moiety to an oligonucleotide comprising reacting a reporter moiety having an oxime forming nucleophile substituent with an oxo substituted reactant coupled to a solid support to form an oxime bond between the reporter moiety and the reactant. The reporter moieties include, but are not limited to, quenchers, fluorophores, biotin, digoxigenin, peptides and proteins. The invention also provides an oligonucleotide labeled with at least two different reporter moieties.

This invention further provides novel azo quenchers having the general formula shown below in Formula (I):

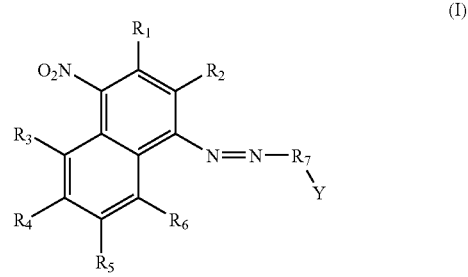

Each of $R_{1-6}$ is individually selected from the group consisting of hydrogen; electron withdrawing groups such as halogens, $NO_2$, $SO_3R_S$, $SO_2N(R_N)_2$, CN, CNS, keto, alkoxy groups; $C_1$-$C_{10}$ alkyl groups; aryl groups; and heteroaryl groups. $R_N$ and $R_S$ can be $C_1$-$C_{10}$ alkyl groups, which may be saturated or unsaturated, branched or unbranched, and substituted or unsubstituted, or aryl groups, which may be substituted or unsubstituted. Suitable substituents include electron withdrawing groups, such as those described above.

$R_7$ can be any aryl group that can be joined to the conjugated ring system by an azo bond to form a compound that is capable of quenching the fluorescence of a fluorophore. Suitable aryl groups include phenyl, naphthyl, benzyl, xylyl, toluoyl, pyridyl and anilinyl, among other groups. $R_7$ can be substituted or derivatized with at least one linking group for linking the quencher compound to other compounds of interest.

Y is a nucleophile-containing group capable of reacting with an oxo group to form an oxime bond, such as aminooxy or hydrazine. In addition, the $R_1/R_2$ pair, $R_3/R_4$ pair, $R_4/R_5$ pair and $R_5/R_6$ pair can be combined to form ring structures having five or six ring members. These ring structures can be substituted with hydrogen, heteroatom-substituted alkyl, halogen, alkenyl, alkoxy, alkoxy-alkyl, hydroxyl, trifluoromethyl, cyano, nitro, acyl, acyloxy, amino, alkylamino, dialkylamino, carboxyl, carbalkoxyl, carboxamido, mercapto, sulfamoyl, phenyl, and napthyl.

In addition, this invention provides an oligonucleotide labeled with the novel quencher as well as a method of detecting hybridization of oligonucleotides using the labeled oligonucleotide.

The invention provides compositions comprising a quencher linked to a compound selected from the group consisting of an antigen, a steroid, a vitamin, a drug, a hapten, a metabolite, a toxin, an environmental pollutant, an amino acid, a protein, a carbohydrate, a solid support, a linker, and a lipid, wherein the quencher is attached to the compound via an oxime bond. The invention further provides compositions comprising labeled oligonucleotides and solid supports. The invention also provides kits comprising at least one composition of the present invention.

DETAILED DESCRIPTION OF THE INVENTION

The invention provides a novel method of labeling oligonucleotides with reporter moieties during synthesis of the oligonucleotide. The method permits the attachment of several different reporter moieties to a single oligonucleotide.

For the purposes of this invention, the term "reporter moiety" refers to a substituent that allows detection, either directly or indirectly, of a compound at low concentrations. Suitable reporter moieties include, but are not limited to, (1) enzymes, which produce a signal detectable, for example, by colorimetry, fluorescence or luminescence, such as horseradish peroxidase, alkaline phosphatase, beta-galactosidase or glucose-6-phosphate dehydrogenase; (2) chromophores, such as fluorescent, luminescent or dye compounds; (3) groups with an electron density which can be detected by electron microscopy or through their electrical property, such as by conductivity, amperometry, voltametry, or impedance measurements; and (4) groups which can be detected using optical methods, such as diffraction, surface plasma resonance or contact angle variation, or physical methods, such as atomic force spectroscopy, or the tunnel effect. Other suitable reporter moieties include, but are not limited to, biotin, digoxigenin, peptides, proteins, antibodies, glycoproteins, and sugars.

In one embodiment, the method comprises forming an O-substituted oxime ("oxime") bond between a reporter moiety having a nucleophile capable of forming an oxime bond with an oxo group (also referred to as a nucleophile containing reporter moiety) and an oxo-substituted reactant. The oxime bond is completely orthogonal to reactions during phosphoramidite oligonucleotide synthetic cycle and can be used as a universal method for introduction of multiple modifications into an oligonucleotide. The oxime bond may be used to introduce almost any modification into an oligonucleotide during synthesis or prior to synthesis by modification of the solid support. The bond is unexpectedly stable, and remains intact during thermocycling. This method also permits the introduction of multiple different reporter moieties into an oligonucleotide.

Figure 3:
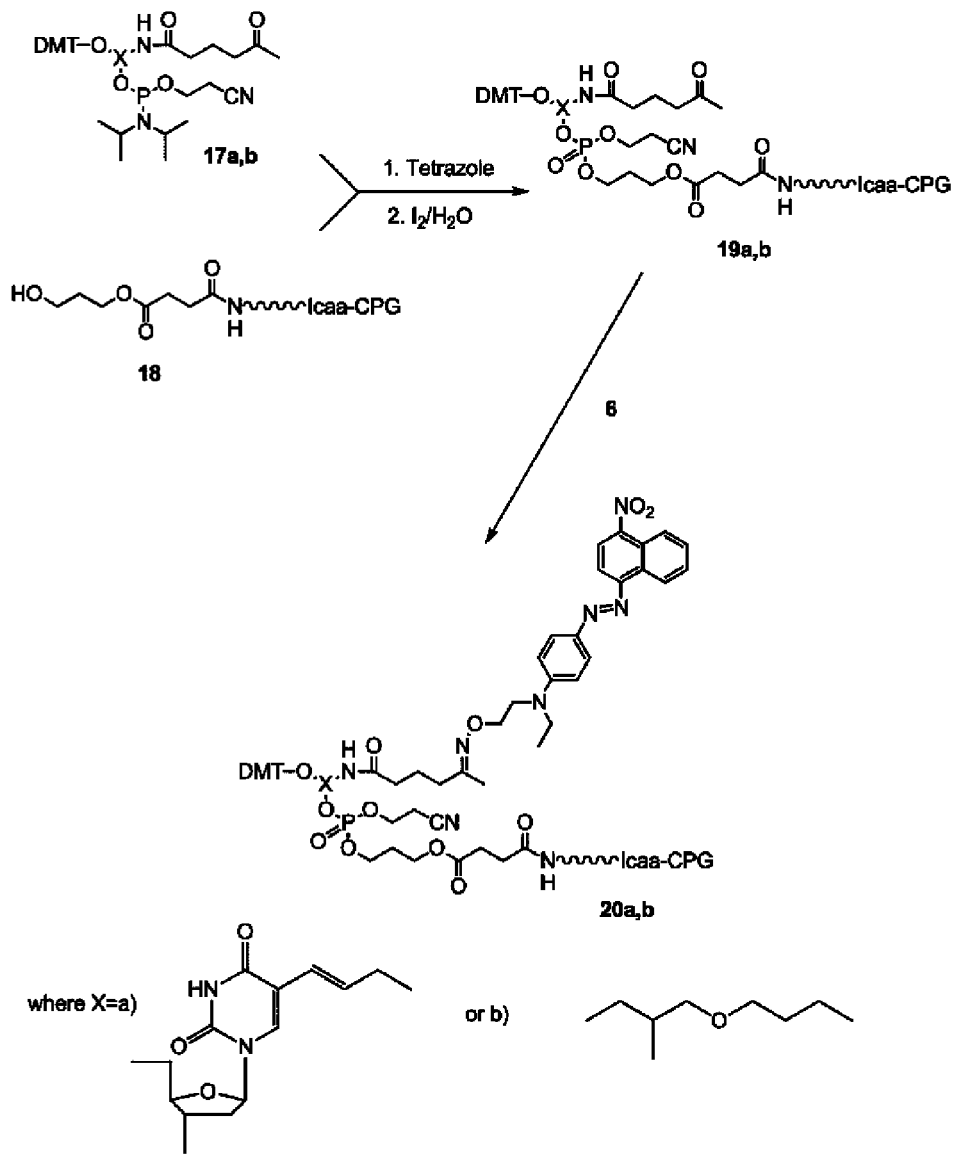
FIG. 3 shows the synthesis of aminooxy conjugated controlled pore glass supports.
Figure 4:
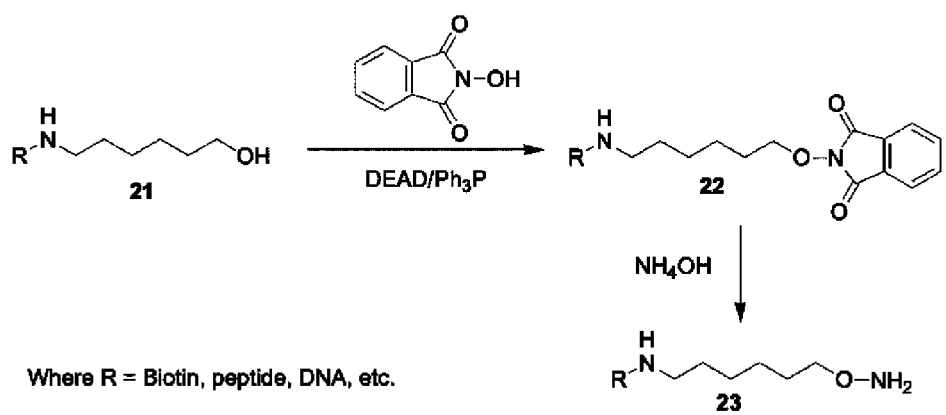
FIG. 4 shows the introduction of the aminooxy group into a reporter moiety that is stable to basic conditions.
Figure 5:
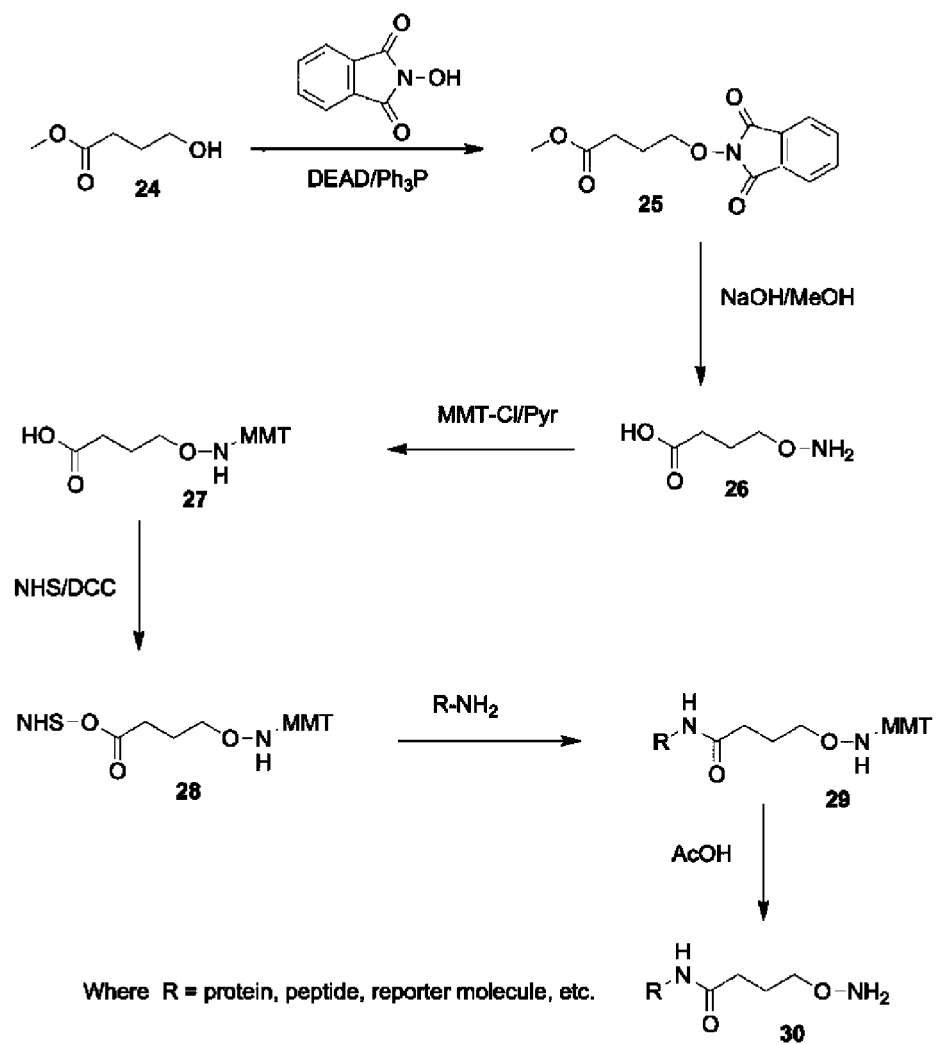
FIG. 5 shows the introduction of the aminooxy group into a base labile reporter moiety.

The oxo-substituted reactant can be an oxo-substituted oligonucleotide which is linked to a solid support, an oxo-substituted nucleotide, an oxo-substituted nucleoside, an oxo-substituted nucleoside phosphoramidite, or a composition of Formula (II):

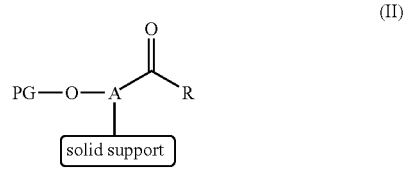

wherein R is H or alkyl, PG is a hydroxyl protecting group, such as those commonly used in oligonucleotide synthesis, e.g. dimethoxytrityl (DMT), monomethoxytrityl (MMT), or trityl, and A is a linker used to attach an oligonucleotide to a solid support during synthesis of the oligonucleotide, such as the phosphate linkers, shown in 20a and 20b of FIG. 3. Suitably, the alkyl is selected from a $C_{1-6}$ alkyl group, which is substituted or unsubstituted, branched or unbranched, and saturated or unsaturated. Suitable substituents include, but are not limited to, alkoxy, hydroxyl, cyano, amino, alkylamino, dialkylamino, halogen, alkylthio, and thiol. The oxo-substituted nucleotide and oxo-substituted nucleoside can be attached to a solid support.

The oxo-substituted oligonucleotides, oxo-substituted nucleotides, oxo-substituted nucleosides, and oxo-substituted nucleoside phosphoramidites for use in the present invention include those containing the traditional nucleobases, such as adenine, guanine, cytosine, uracil and thymine, and those containing modified nucleobases.

The term "solid support" refers to any support that is compatible with oligonucleotide synthesis. For example, the following are suitable: glass, controlled pore glass, polymeric materials, polystyrene beads, coated glass, and the like.

In another embodiment, the method permits incorporation of an oxo-substituted nucleotide into an oligonucleotide followed by reaction with a reporter moiety having a nucleophilic substituent capable of forming an oxime bond with the oxo group. The reporter moiety can be added immediately after the oxo-substituted nucleotide is added to the oligonucleotide or the reporter moiety can be added after additional nucleotides or oxo-substituted nucleotides have been added to the oligonucleotide. In another suitable embodiment, the novel method permits internal incorporation of a reporter moiety into an oligonucleotide as a reporter moiety substituted nucleotide which is incorporated into the oligonucleotide using standard phosphoramidite chemistry.

In another embodiment, the nucleophile containing reporter moiety can be reacted with an oxo-substituted reactant. The resulting composition, a reporter moiety substituted reactant, is then used to derivatize a solid support, as in Example 3, and the derivatized support can serve as the foundation for oligonucleotide synthesis by standard methods. Although Example 3 demonstrates the attachment of an azo quencher compound to controlled pore glass, the method is more generally applicable to the attachment of a reporter moiety to any solid support that contains free reactive electrophile groups, including ketones and aldehydes. The solid support bound reporter moiety can be used conveniently in conjunction with automated oligonucleotide synthesizers to directly incorporate the reporter moiety into oligonucleotides during their synthesis.

The present method allows for multiple reporter moieties to be introduced into a single oligonucleotide. The reporter moieties may be the same or different. Use of different reporter moieties on a single oligonucleotide allows detection of multiple signals using a single oligonucleotide. Detection may be simultaneous or sequential.

The invention also provides novel azo compounds that are useful as fluorescence quenchers. The quenchers of this invention, which release energy absorbed from fluorophores without emitting light, i.e. are "dark quenchers", have the general formula shown below in Formula (I).

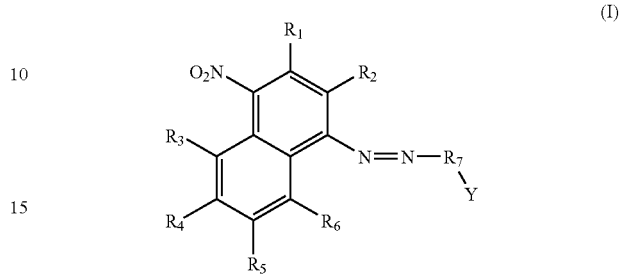

Each of $R_{1-6}$ is individually selected from the group consisting of hydrogen, electron withdrawing groups such as halogens, $NO_2$, $SO_3R_S$, $SO_2N(R_N)_2$, CN, CNS, keto, and alkoxy groups, $C_1$-$C_{10}$ alkyl groups, aryl groups, and heteroaryl groups. $R_N$ and $R_S$ can be $C_1$-$C_{10}$ alkyl groups, which may be branched or unbranched and saturated or unsaturated, and substituted or unsubstituted, and aryl groups, which may be substituted or unsubstituted. Suitable substituents include electron withdrawing groups such as those described above.

$R_7$ can be any aryl group that can be joined to the conjugated ring system by an azo bond to form a compound that is capable of quenching the fluorescence of a fluorophore. Suitable aryl groups include phenyl, naphthyl, benzyl, xylyl, toluoyl, pyridyl, and anilinyl, among other groups. $R_7$ can be substituted or derivatized with at least one linking group for linking the quencher compound to other compounds of interest.

Y is a nucleophile-containing group capable of reacting with an oxo group to form an oxime bond, such as aminooxy or hydrazine. In addition, any one of the $R_1/R_2$ pair, $R_3/R_4$ pair, $R_4/R_5$ pair and $R_5/R_6$ pair can be combined to form ring structures having five or six ring members. These ring structures can be substituted with hydrogen, heteroatom-substituted alkyl, halogen, alkenyl, alkoxy, alkoxy-alkyl, hydroxyl, trifluoromethyl, cyano, nitro, acyl, acyloxy, amino, alkylamino, dialkylamino, carboxyl, carbalkoxyl, carboxamido, mercapto, sulfamoyl, phenyl, and napthyl.

In addition, reactive substituents at $R_{1-6}$, such as amino, hydroxyl, and carboxyl groups, can be attached to linking groups or other molecules of interest.

For purposes of this invention, the term "linking group" refers to a chemical group that is capable of reacting with a "complementary functionality" of a reagent, e.g., to the ketone group of a phosphoramidite, to form a bond that connects the azo quenching compound of Formula (I) to the reagent. See R. 35 Haugland (1992) Molecular Probes Handbook of Fluorescent Probes and Research Chemicals, Molecular Probes, Inc., disclosing numerous modes for conjugating a variety of dyes to a variety of compounds, which is incorporated herein by reference.

In one embodiment, $R_7$—Y is the compound of Formula (III) where the aryl ring is an anilinyl group which can be substituted with various groups at positions L and L'.

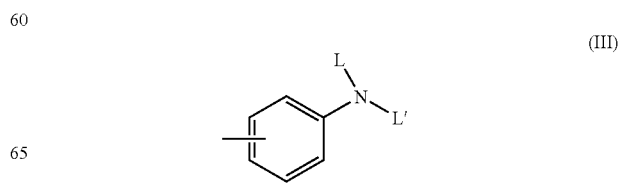

L and L' are independently selected from the group consisting of substituted or unsubstituted $C_{1-10}$ alkyl and nucleophile-containing $C_{1-10}$ alkyl groups, wherein the $C_{1-10}$ alkyl groups are saturated or unsaturated. For example, in one embodiment, one of L or L' can be a nonreactive group (i.e., one that does not contain a nucleophile and cannot be modified to contain a nucleophile), such as an alkyl group, preferably an ethyl group, and the other can be a reactive group, such as a hydroxyethyl group which can be modified further to a nucleophilic group such as aminooxy to facilitate linking the quencher to other molecules of interest. One of skill in the art would recognize that hydroxy alkyl chains of any length could be used to modify the anilinyl group.

A suitable embodiment of Formula (III) is shown in Formula (IV) below.

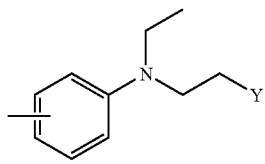
(IV)

wherein Y is a nucleophile capable of reacting with an oxo group to form an oxime bond.

In one embodiment of Formula (I), the azo quencher compound has the structure of Formula (V), wherein Y is an aminooxy group.

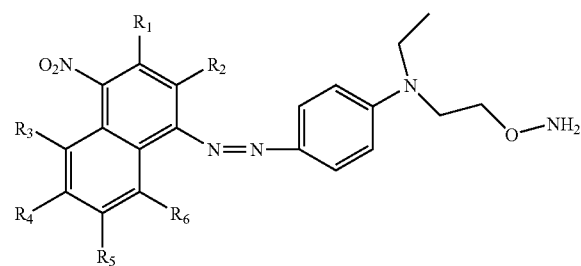
(V)

Suitable azo quencher precursor compounds have a primary amino group and have the general structure of Formula (VI). Specific embodiments of Formula (VI) include compounds 1 and 2.

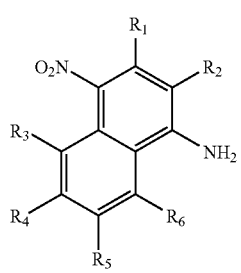
(VI)

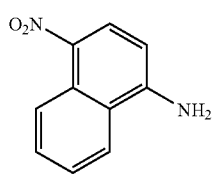
1

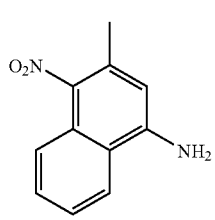
2

The azo quenchers of Formula (I) are suitable for incorporation into oligonucleotides as is discussed above. The azo quenchers of Formula (I) can be linked to a variety of other useful compounds, provided that suitable reactive groups are present on those compounds. Such compounds include antigens, antibodies, steroids, vitamins, drugs, haptens, metabolites, toxins, environmental pollutants, amino acids, proteins, carbohydrates, lipids, and the like.

Figure 15:
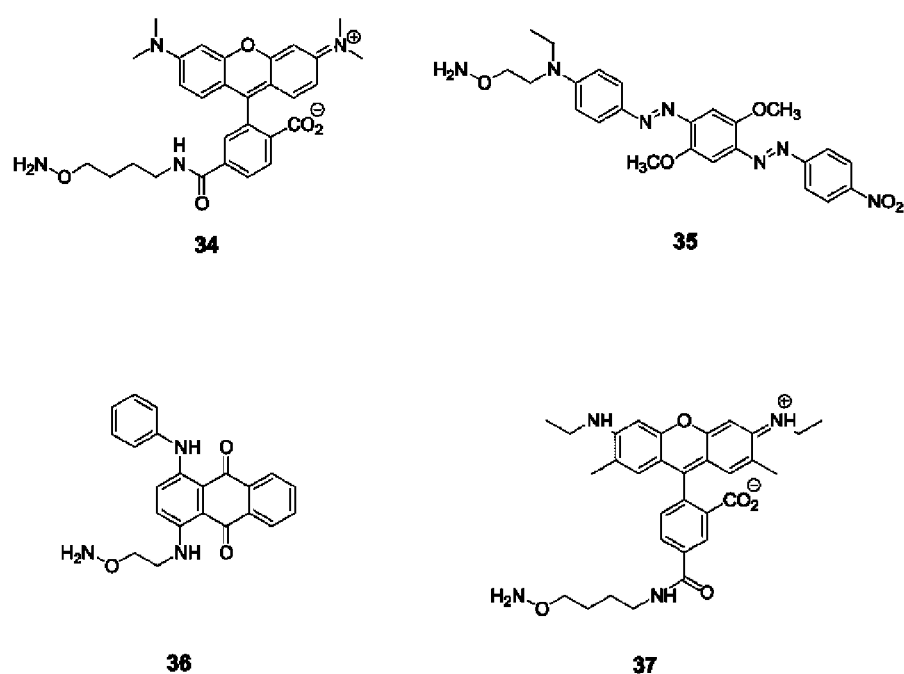
FIG. 15 shows examples of aminooxy substituted reporter moieties.

Examples of other aminooxy substituted reporter moieties are shown in FIG. 15.

The invention also is directed to oligonucleotide compositions containing dye pairs, which include one of the disclosed quencher compounds and a fluorophore that fluoresces on exposure to light of the appropriate wavelength. Suitable fluorophores in the dye pair are those that emit fluorescence that can be quenched by the quencher of the dye pair. In certain embodiments, the dye pair can be attached to a single compound, such as an oligonucleotide. In other embodiments, the fluorophore and the quencher can be on different compounds.

A wide variety of reactive fluorophores are known in the literature and can be used with a corresponding quencher. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorophores include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorophores also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Other fluorophores include coumarins, such as 3-phenyl-7-isocyanatocoumarin; acridines, such as 9-isothiocyanatoacridine and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H,5H,11H,15H-Xantheno[2,3,4-ij:5,6,7-i'j'] diquinolizin-18-ium, 9-[2(or 4)-[[[6-[2,5-dioxo-1-pyrrolidinyl]oxy]-6-oxohexyl]amino]sulfonyl]-4(or 2)-sulfophenyl]-2,3,6,7,12,13,16,17-octahydro-inner salt (TR or Texas Red);

BODIPY™ dyes; benzoxaazoles; stilbenes; pyrenes; and the like. The fluorescent emission of certain fluorophores is provided below.

| Fluorophore | Emission Max |
| --- | --- |
| 6-Carboxyfluorescein (6-FAM) | 520 nm |
| Tetrachlorofluorescein (TET) | 536 nm |
| Hexachlorofluorescein (HEX) | 556 nm |
| Cy3 | 570 nm |
| Tetramethylrhodamine (TAMRA) | 580 nm |
| Cy3.5 | 596 nm |
| Carboxy-x-rhodamine (ROX) | 605 nm |
| Texas Red | 610 run |
| Cy5 | 667 nm |
| Cy5.5 | 694 nm |

The quencher of Formula (I) is capable of absorbing the fluorescent energy in the range of about 500 to about 620 nm and therefore can be used to quench the fluorescence of fluorescein through Texas Red.

Many suitable forms of fluorophores are available and can be used depending on the circumstances. With xanthene compounds, substituents can be attached to xanthene rings for bonding with various reagents, such as for bonding to oligonucleotides. For fluorescein and rhodamine dyes, appropriate linking methodologies for attachment to oligonucleotides have also been described. See, for example, Khanna et al. U.S. Pat. No. 4,439,356, which is incorporated herein by reference; Marshall (1975) Histochemical J., 7:299-303, which is incorporated herein by reference; Menchen et al., U.S. Pat. No. 5,188,934, which is incorporated herein by reference; Menchen et al., European Patent Application No. 87310256.0, which is incorporated herein by reference; and Bergot et al., International Application PCT/U590/05565, which is incorporated herein by reference. Other quenchers could potentially be incorporated into an oligonucleotide using the method of the present invention. Some of these are shown in Table 1 below.

TABLE 1

| Quencher Name/ODN modification | Chemical structure | $\lambda_{max}$ (nm) |
| --- | --- | --- |
| Dabcyl | 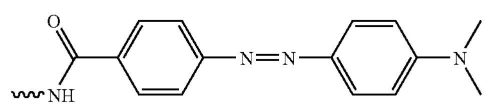 | 474 |
| Eclipse (Disperse Red 13) | 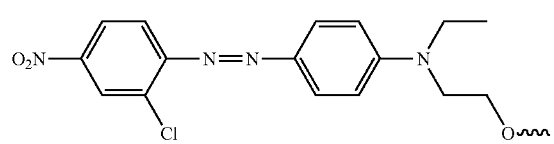 | 522 |
| 3'-BHQ-1 | 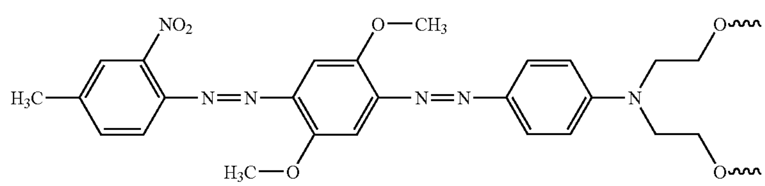 | 534 |
| 3'-BHQ-2 | 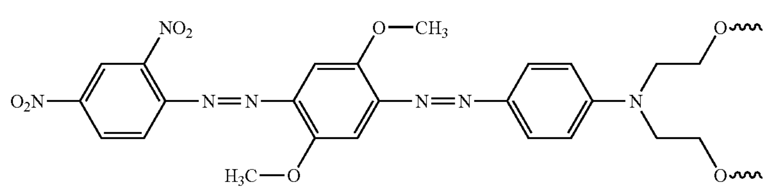 | 579 |
| 3'-BHQ-3 | 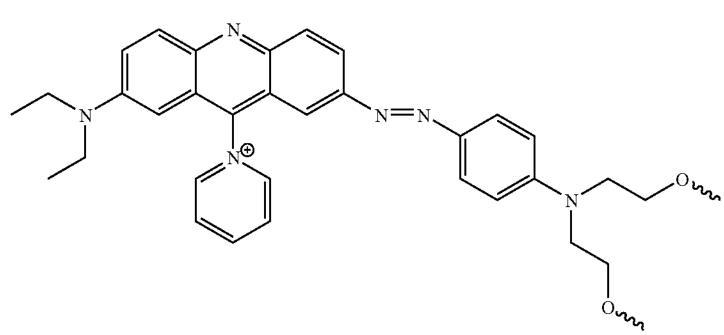 | 672 |

TABLE 1-continued

| Quencher Name/ODN modification | Chemical structure | $\lambda_{max}$ (nm) |
|---|---|---|
| QSY7 | 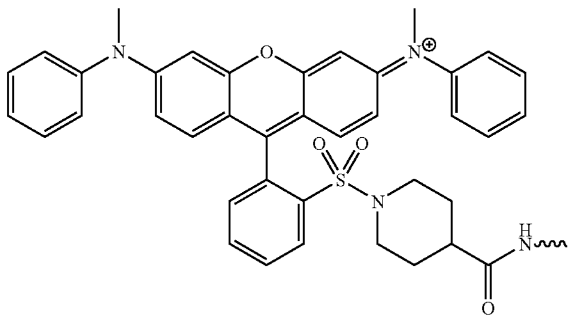 | 560 |
| QSY9 | 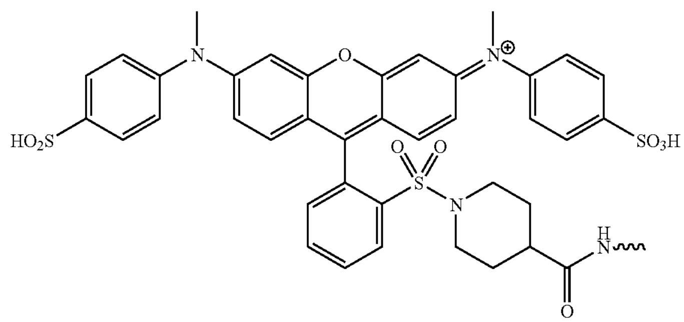 | 661 |
| QSY21 | 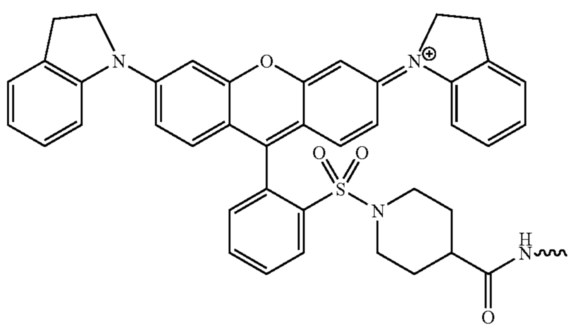 | 661 |
| QSY35 | 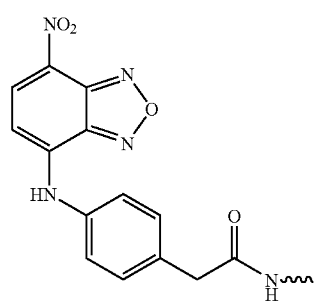 | 475 |

Suitably, when the dye pair is in a configuration in which fluorophore is effectively quenched by the quencher dye, its fluorescence is reduced by at least a factor of 80%, and more preferably by 90%, 95%, or 98%, when compared to its fluorescence in the absence of quenching. High levels of quenching allow for the preparation of oligonucleotide probes having a high signal to noise ratio which is defined as the amount of signal present when the composition is in its maximal unquenched state (signal) versus its maximally quenched state (noise).

Probes having a high signal to noise ratio are desirable for the development of highly sensitive assays. To measure signal to noise ratios relative fluorescence is measured in a configuration where the quencher and fluorophore are within the Förster distance and the fluorophore is maximally quenched (background fluorescence or "noise") and compared with the fluorescence measured when fluorophore and quencher are separated in the absence of quenching ("signal"). The signal to noise ratio of a dye pair of the invention will generally be at least about 2:1 but generally is higher. Signal to noise ratios are generally affected by the fluorophore-quencher pair, the quality of the synthesis, and the oligonucleotide sequence.

Oligonucleotide probes that include a dye pair can be used to detect target oligonucleotides. In one method, the individual components of a dye pair can be on opposing, hybridizable, self-complementary segments of a single oligonucleotide such that when the oligonucleotide hybridizes to itself in the absence of exogenous sequences, FRET occurs. The oligonucleotide probe is constructed in such a way that the internal hybridizing is disrupted and fluorescence can be observed when the oligonucleotide probe hybridizes to a complementary target oligonucleotide. Such an oligonucleotide probe can be used to rapidly detect target oligonucleotides having sequences that bind to the oligonucleotide probe. In another embodiment, a composition comprises two biomolecules, such as oligonucleotides, with a fluorophore attached to one of the biomolecules and a quencher attached to the other.

Oligonucleotide probes lacking self-complementarity can also be utilized in a similar manner. For example, a quencher and fluorophore can be placed on an oligonucleotide that lacks the self-hybridizing property such that the random-coil conformation of the oligonucleotide keeps the fluorophore and quencher within a suitable distance for fluorescence quenching. Such oligonucleotides can be designed so that when they hybridize to desired target oligonucleotides the fluorophore and quencher are further apart and fluorescence can be observed.

Other DNA binding formats are also possible. For example, two oligonucleotide probes can be designed such that they can hybridize adjacent to each other on a contiguous length of a target oligonucleotide. The two probes can be designed such that when they are hybridized to the target oligonucleotide, a quencher on one of the oligonucleotide probes is within a sufficient proximity to a fluorophore on the other oligonucleotide probe for FRET to occur. Binding of the oligonucleotide probes to the target oligonucleotide can be followed as a decrease in the fluorescence of the fluorophore.

Alternatively, a set of oligonucleotides that hybridize to each other can be configured such that a quencher and a fluorophore are positioned within the Förster distance on opposing oligonucleotides. Incubation of such an oligonucleotide duplex with another oligonucleotide that competes for binding of one or both of the oligonucleotides would cause a net separation of the oligonucleotide duplex leading to an increase in the fluorescent signal of the fluorophore. To favor binding to the polymer strands, one of the oligonucleotides could be longer or mismatches could be incorporated within the oligonucleotide duplex.

These assay formats can easily be extended to multi-reporter systems that have mixtures of oligonucleotides in which each oligonucleotide has a fluorophore with a distinct spectrally resolvable emission spectrum. The binding of individual oligonucleotides can then be detected by determining the fluorescent wavelengths that are emitted from a sample. Such multi-reporter systems can be used to analyze multiple hybridization events in a single assay.

Oligonucleotides can also be configured with the disclosed quenchers such that they can be used to monitor the progress of PCR reactions without manipulating the PCR reaction mixture (i.e., in a closed tube format). The assay utilizes an oligonucleotide that is labeled with a fluorophore and a quencher in a configuration such that fluorescence is substantially quenched. The oligonucleotide is designed to have sufficient complementarity to a region of the amplified oligonucleotide so that it will specifically hybridize to the amplified product. The hybridized oligonucleotide is degraded by the exonuclease activity of Taq polymerase in the subsequent round of DNA synthesis. The oligonucleotide is designed such that as the oligomer is degraded, one of the members of the dye pair is released and fluorescence from the fluorophore can be observed. An increase in fluorescence intensity of the sample indicates the accumulation of amplified product.

Ribonucleic acid polymers can also be configured with fluorophores and quenchers and used to detect RNase. For example, a dye pair can be positioned on opposite sides of an RNase cleavage site in an RNase substrate such that the fluorescence of the fluorophore is quenched. Suitable substrates include oligonucleotides that have a single-stranded region that can be cleaved and that have at least one internucleotide linkage immediately 3' to an adenosine residue, at least one internucleotide linkage immediately 3' to a cytosine residue, at least one internucleotide linkage immediately 3' to a guanosine residue and at least one internucleotide linkage next to a uridine residue and optionally can lack a deoxyribonuclease-cleavable internucleotide linkage. To conduct the assay, the substrate can be incubated with a test sample for a time sufficient for cleavage of the substrate by a ribonuclease enzyme, if present in the sample. The substrate can be a single-stranded oligonucleotide containing at least one ribonucleotide residue at an internal position. Upon cleavage of the internal ribonucleotide residue, the fluorescence of the fluorophore, whose emission was quenched by the quencher, becomes detectable. The appearance of fluorescence indicates that a ribonuclease cleavage event has occurred, and, therefore, the sample contains ribonuclease activity. This test can be adapted to quantitate the level of ribonuclease activity by incubating the substrate with control samples containing known amounts of ribonuclease, measuring the signal that is obtained after a suitable length of time, and comparing the signals with the signal obtained in the test sample.

The invention also provides kits that comprise a labeled oligonucleotide or an azo quencher of the present invention. The kit can also contain instructions for use. Such kits can be useful for practicing the described methods or to provide materials for synthesis of the compositions as described. Additional components can be included in the kit depending on the needs of a particular method. For example, where the kit is directed to measuring the progress of PCR reactions, it can include a DNA polymerase. Where a kit is intended for the practice of the RNase detection assays, RNase-free water could be included. Kits can also contain negative and/or positive controls and buffers.

The following examples further illustrate the invention but, of course, should not be construed as in any way limiting its scope. In particular the following examples demonstrate synthetic methods for obtaining the compounds of the invention. Starting materials useful for preparing the compounds of the invention and intermediates thereof, are commercially available or can be prepared from commercially available materials using known synthetic methods and reagents. All oligonucleotide sequences are written from the 5'-terminus on the left to the 3'-terminus on the right.

Example 1

Synthesis of aminooxy activated
(1-nitro-4-naphthylazo)-N,N-diethanolaniline
quencher (6)

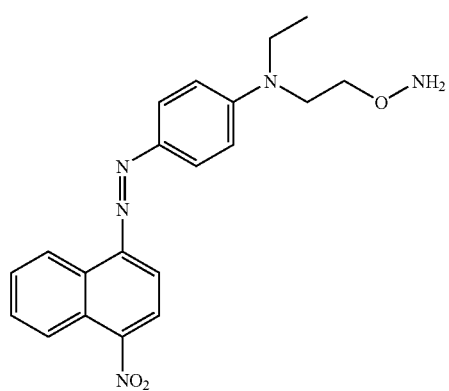

Figure 1:
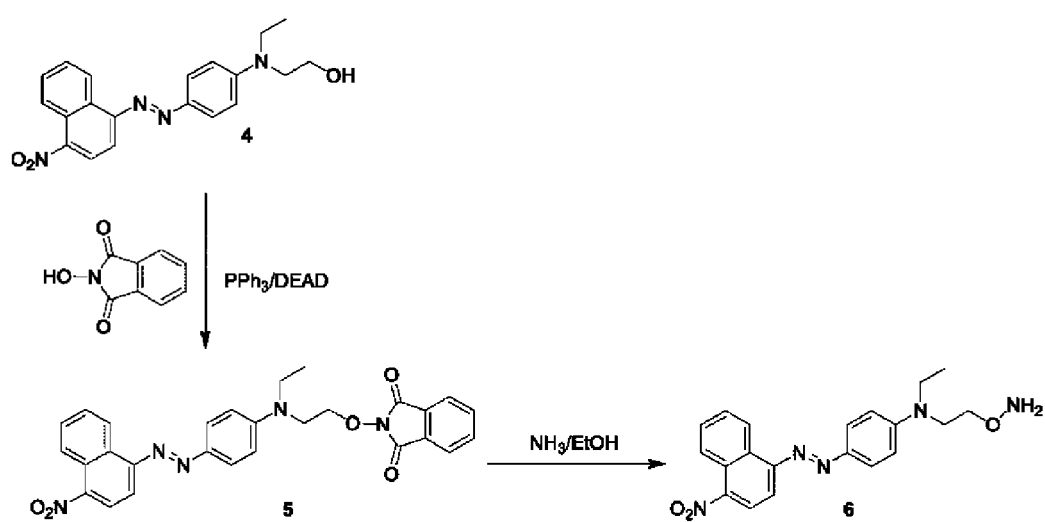
FIG. 1 shows the synthesis of a compound of Formula (I).

Synthesis was performed as shown in Scheme 1 in FIG. 1. To the solution of 0.36 g (0.1 mmol) alcohol (4), 0.17 g (0.1 mmol) N-hydroxy-phthalimide, and 0.27 g (0.1 mmol) of triphenylphosphine in 10 mL of THF was added 0.18 mL (0.1 mmol) of diethylazodicarboxylate (DEAD). After overnight stirring the reaction mixture was concentrated under diminished pressure. Flash chromatography with 1:4 EtOAc/hexanes provided 150 mg of (5). TLC: $R_f$ 0.75 (EtOAc/hexanes—60/40). $^1$H NMR (CDCl$_3$) δ 9.04 (d, J=8.4 Hz, 1H), 8.68 (d, J=8.4 Hz, 1H), 8.34 (d, J=8.4 Hz, 1H), 8.03 (d, J=8 Hz, 2H), 7.7-7.9 (m, 7H), 6.85 (d, J=8 Hz, 2H), 4.46 (t, J=7.5 Hz, 2H), 3.92 (t, J=7.5 Hz 2H), 3.72 (q, J=8 Hz, 2H), 1.34 (t, J=8 Hz 3H).

The solution of 10 mg (5) in 2 mL of concentrated ammonia solution in ethanol was incubated overnight at 55° C. The solvent was removed under diminished pressure to provide 6) that was used further without purification.

Example 2

Synthesis of Ketone Phosphoramidite (16)

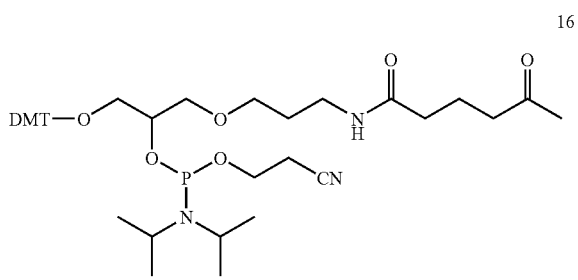

Figure 2:
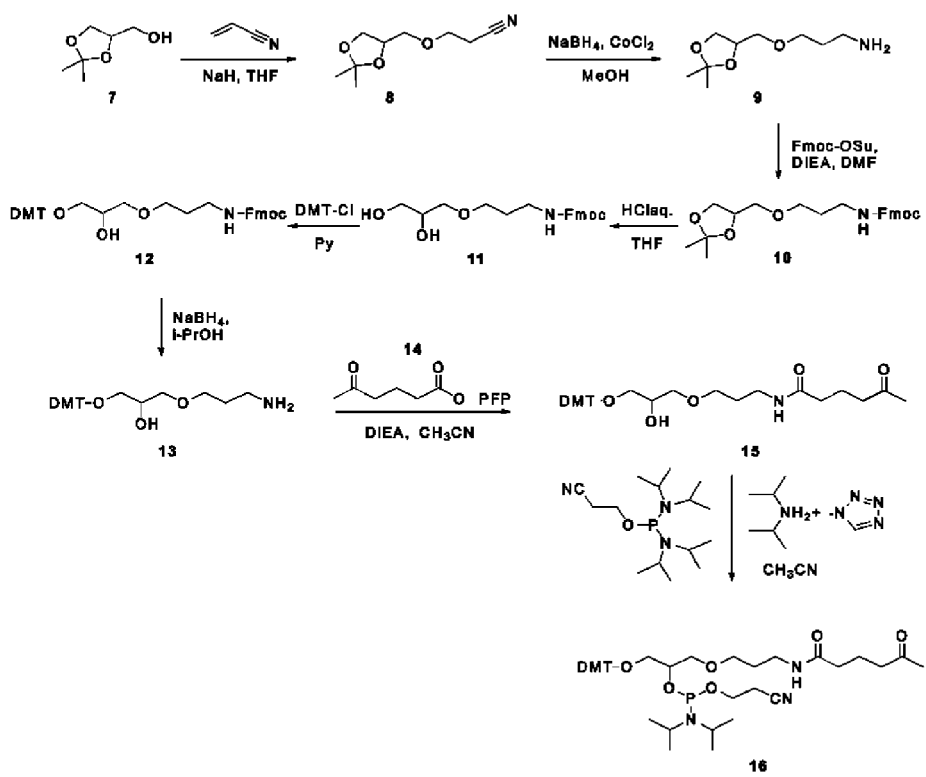
FIG. 2 shows the synthesis of a ketone phosphoramidite.

Synthesis was performed as shown in Scheme 2 of FIG. 2.

N-Fmoc-3-aminopropyl solketal (10): 3-Aminopropyl solketal (9) was synthesized starting from commercially available solketal (7) according to the procedure of Misiura et al (Misiura, K., Durrant, I., Evans, M. R., Gait, M. J. (1990) Nucleic Acids Research, v. 18, No. 15, pp. 4345-4354, which is incorporated herein by reference). (9) was used crude without vacuum distillation for the next step. The crude product (9) (12.85 g; 68 mmol) was dissolved in dry CH$_3$CN (100 mL) with stirring. NaHCO$_3$ (4.2 g; 50 mmol) was added followed by Fmoc-OSu (16.9 g; 50 mmol). The reaction mixture was stirred at room temperature overnight. The solvent was evaporated and the oily residue was partitioned between EtOAc (500 mL) and 5% NaHCO$_3$ (150 mL). The organic layer was separated and washed with 5% NaHCO$_3$ (2×150 mL), brine (150 mL), and dried over anhydrous Na$_2$SO$_4$. The product (10) was isolated by flash chromatography on a silica gel column (5×20 cm) loading from EtOAc:CH$_2$Cl$_2$:petroleum ether (PE) (15:15:70) and eluting with EtOAc:CH$_2$Cl$_2$:PE (1:1:2). The isolated product (10) had $R_f$ of 0.4 by TLC in EtOAc:CH$_2$Cl$_2$:PE (1:1:1). Yield: 20.95 g of oil. $^1$H NMR (CDCl$_3$) δ 1.35 (s, 3H), 1.45 (s, 3H), 1.81 (m, 2H), 3.34 (q, 2H), 3.47-3.60 (m, 4H), 3.75 (dd, 1H), 4.07 (dd, 1H), 4.22-4.32 (m, 2H), 4.42 (d, 2H), 5.29 (br. t, 1H), 7.33 (dt, 2H), 7.42 (t, 2H), 7.62 (d, 2H), 7.78 (d, 2H).

1-O—(N-Fmoc-3-aminopropyl)glycerol (11): Crude compound (10) (5 g; 12.1 mmol) was dissolved in THF (15 mL) and treated with 2M HCl (5 mL). The resulting emulsion was shaken at room temperature with occasional sonication until it became homogeneous. It was then left at room temperature for additional hour. The reaction mixture was concentrated in vacuum, and the resulting oil was co-evaporated with absolute EtOH (3×20 mL). The reaction product ($R_f$ of ~0.3 in EtOAc:CH$_2$Cl$_2$:MeOH (10:10:1)) was isolated by silica gel chromatography (5×20 cm) using a gradient 0-5% MeOH in EtOAc:CH$_2$Cl$_2$ (1:1). Fractions containing pure product were pooled and concentrated to give oily residue, which crystallized upon vacuum drying. Yield: 2.64 g of a white solid (11). $^1$H NMR (DMSO-d6) δ 1.63 (m, 2H), 3.05 (q, 2H), 3.25-3.41 (m, 6H), 3.53-3.60 (m, 1H), 4.21 (t, 1H), 4.30 (d, 2H), 4.47 (t, 1H), 4.60 (d, 1H), 7.27 (t, 1H), 7.33 (dt, 2H), 7.42 (t, 2H), 7.69 (d, 2H), 7.89 (d, 2H).

1-O-DMT-3-O—(N-Fmoc-3-aminopropyl)glycerol (12): 1-O—(N-Fmoc-3-aminopropyl)glycerol (11) (2.64 g; 7.1 mmol) was dissolved in dry pyridine (50 mL) and treated with DMT-Cl (2.65 g; 7.8 mmol). The reaction mixture was stirred at room temperature overnight and quenched with MeOH (5 mL). It was then concentrated to oil under reduced pressure. The residue was dissolved in EtOAc (~300 mL) and extracted with saturated NaHCO$_3$ (3×100 mL) followed by brine (100 mL). The organic phase was separated, dried over anhydrous Na$_2$SO$_4$ and concentrated to oil. The product (12) was isolated by silica gel chromatography using a gradient 33-66% EtOAc in petroleum ether ("PE"). Yield: 4.03 g (84%) of white foam (12). TLC showed one spot at $R_f$~0.6 in EtOAc:PE (2:1). $^1$H NMR (CDCl$_3$) δ 1.68-1.80 (m, 2H), 2.57 (br d, 1H), 3.17-3.34 (m, 4H), 3.43-3.61 (m, 4H), 3.79 (s, 6H), 3.93-4.00 (m, 1H), 4.22 (t, 1H), 4.41 (d, 2H), 5.20 (br t, 1H), 6.82-6.86 (m, 4H), 7.21-7.46 (m, 13H), 7.61 (d, 2H), 7.77 (d, 2H).

1-O-DMT-3-O-(3-aminopropyl)glycerol (13): Compound (12) (3.82 g; 5.67 mmol) was dissolved in i-PrOH (100 mL) and sodium borohydride (4 g) was added in portions with stirring. The suspension was heated at 70° C. for 2 hours. TLC analysis in EtOAc:TEA (99:1) revealed the disappearance of the starting material ($R_f$~0.75) and formation of deprotected product at the start. The reaction was carefully quenched with 10% sodium hydroxide (32 mL), transferred into a reparatory funnel and partitioned with 300 mL of ethyl acetate. The organic phase was separated, washed with saturated NaHCO$_3$ (3×100 mL) followed by brine (100 mL), and dried over sodium sulfate. It was then concentrated in vacuum to give oily residue, which was co-evaporated with dry acetonitrile (50 mL). This crude material (13) was used in the next step without further purification.

Pentafluorophenyl 5-oxohexanoate (14): 5-Oxohexanoic acid (2.6 g; 20 mmol) was dissolved in CH$_2$Cl$_2$ (50 mL). N,N-Diisopropylethylamine (10.4 mL, 60 mmol) was added followed by pentafluorophenyl trifluoroacetate (3.61 mL; 21 mmol). The reaction mixture was kept at room temperature for 1 hour and evaporated. The residue was resuspended in EtOAc:Hexanes (1:1) and loaded on a silica gel column (5×20 cm) equilibrated and developed with the same mixture. Fractions containing the product (14) ($R_f$~0.7) were pooled and concentrated to give 4.7 g (79%) of yellowish oil after drying in vacuum. $^1$H NMR (CDCl$_3$) δ 2.05 (m, 2H), 2.18 (s, 3H), 2.61 (t, 2H), 2.74 (t, 2H).

1-O-DMT-3-O—(N-(5-oxohexanoyl)-3-aminopropyl) glycerol (15): The crude product (13) was dissolved in dry CH$_3$CN (50 mL) and treated with N,N-diisopropylethylamine (2.6 mL, 15 mmol) and (14) (1.68 g, 5.67 mmol). The mixture was allowed to react at room temperature for 2 hours.

The reaction mixture was evaporated in vacuum and the residue was reconstituted in EtOAc (50 mL). The product was isolated by silica gel chromatography (4×25 cm) loading from 1% triethylamine (TEA) in EtOAc and eluting with MeOH:EtOAc:TEA (5:95:1). Fractions containing a single component ($R_f$ 0.35) were pooled and concentrated in vacuum to yield the title compound (15) (2.70 g, 85%) as slightly orange oil. $^1$H NMR (DMSO-d6) δ 1.60 (m, 2H), 1.66 (m, 2H), 2.03 (t, 2H), 2.05 (s, 3H), 2.40 (t, 2H), 2.94 (d, 2H), 3.04 (q, 2H), 3.35-3.46 (m, 4H), 3.72-3.79 (m, 7H; OCH$_3$ singlet at 3.74), 4.84 (d, 1H), 6.88 (d, 4H), 7.19-7.42 (m, 9H), 7.72 (t, 1H).

1-O-DMT-3-O—(N-(5-oxohexanoyl)-3-aminopropyl) glycerol 2-O—(N,N-diisopropyl-(2-cyanoethyl)phosphoramidite) (16): Alcohol (15) (1.35 g, 2.4 mmol) and diisopropylammonium tetrazolide (206 mg, 1.2 mmol) were dissolved in anhydrous CH$_3$CN (30 mL) under argon atmosphere. 2-Cyanoethyl N,N,N',N'-tetraisopropylphosphoramidite (0.953 mL, 3.0 mmol) was added with stirring at room temperature, and the reaction mixture was stirred overnight. The solvent was evaporated, the residue was reconstituted in EtOAc (200 mL) and washed with saturated NaHCO$_3$ (3×50 mL) followed with brine (50 mL). The organic layer was dried over anhydrous Na$_2$SO$_4$ and the solvent evaporated under reduced pressure. The oily residue was purified by silica gel chromatography eluting with EtOAc:TEA (95:5). Fractions containing pure product (16), which moves as a double spot on TLC ($R_f$ ~0.55; EtOAc:TEA (95:5)), were pooled and concentrated in vacuum to give 1.74 g of colorless oil (16). $^1$H NMR (DMSO-d6) δ 1.01-1.17 (m, 12H), 1.56 (m, 2H), 1.66 (m, 2H), 2.02 (m, 2H), 2.05 (s, 3H), 2.39 (m, 2H), 2.65 (t, 1H), 2.77 (t, 1H), 2.97-3.16 (m, 4H), 3.36-3.81 (m, 15H; OCH$_3$ singlets at 3.73 and 3.74), 6.88 (m, 4H), 7.19-7.44 (m, 9H), 7.69 (t, 1H). $^{31}$P NMR (DMSO-d6) δ 148.19 and 148.64.

Example 3

Synthesis of aminooxy conjugated CPG supports with (1-nitro-4-naphthylazo)-N,N-diethanolaniline quencher (20a and 20b)

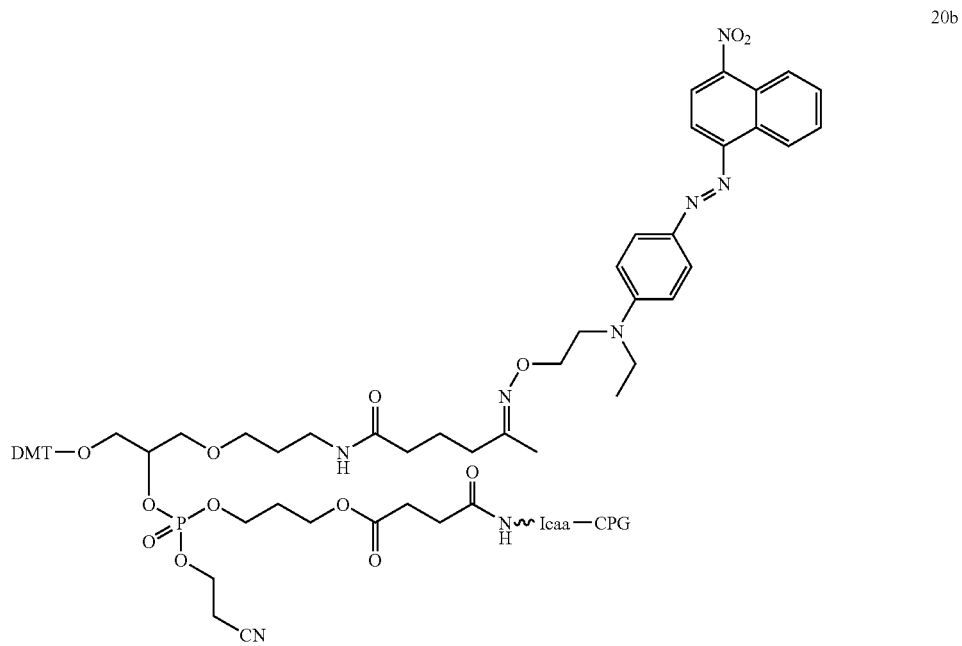

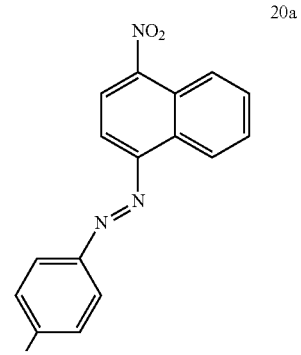

-continued

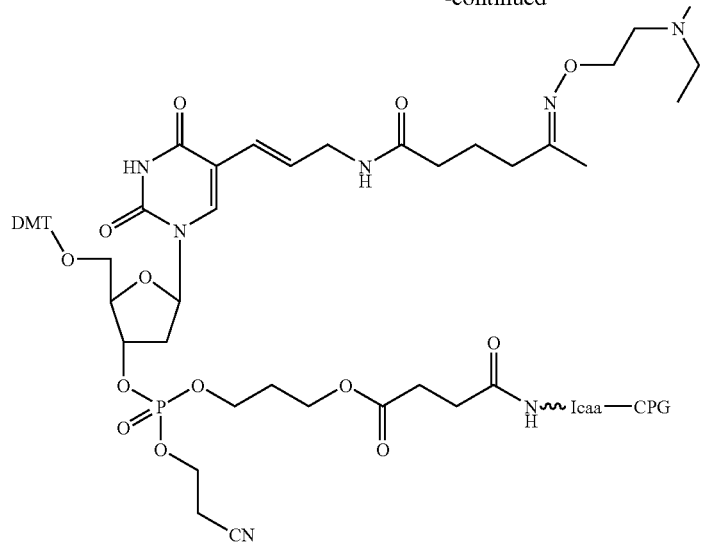

Synthesis was performed as shown in Scheme 3 in FIG. 3.

Synthesis of ketone substituted controlled pore glass (CPG) supports: Spacer C3 CPG (2 g; 44 µmol/g) was placed in a 50 mL peptide synthesis reactor and detritylated by treating with several portions (30 mL) of 3% dichloroacetic acid in dichloromethane (until all the color was washed off the support). It was then washed with $CH_3CN$ (5×50 mL; last two times with anhydrous $CH_3CN$) and "activator" (30 mL; 0.45 M 5-ethylthio-1H-tetrazole in anhydrous. $CH_3CN$) under argon atmosphere. The CPG (18) was then treated with a solution of appropriate phosphoramidite (phosphoramidite (17a) which was synthesized according to published procedure: Dey, S. Shepard, T. (2001) Org Lett, v. 3, pp. 3983-3986) which is incorporated herein by reference; (250 µmol) in 10 mL of anhydrous $CH_3CN$ mixed with 10 mL of "activator" at room temperature for 30 minutes under Ar purge. The reagents were removed by vacuum suction and replaced with a fresh portion. The coupling reaction was repeated; modified CPG was filtered off and washed with $CH_3CN$ (5×30 mL). The solid support was treated with 0.1 M $I_2$ in $THF/Py/H_2O$ (3×30 mL; 5 minutes each treatment), and washed with $CH_3CN$ (5×30 mL). Unreacted hydroxyls were capped by treating with $Ac_2O$:MeIm:Py (10:10:80) (3×30 mL; 5 minutes each treatment). The derivatized CPG (19a) was washed with $CH_3CN$ (5×30 mL), $CH_2Cl_2$ (3×30 mL), and dried in vacuum overnight. DMT-loading was usually above 30 µmol/g.

Attachment of the quencher to ketone substituted support: To the solution of 10 mg quencher (6) was added 0.1 g ketone substituted support (19a) and incubated overnight at room temperature. The resulting support (20a) was filtered and washed with three 1 ml portions of acetonitrile and then used in oligonucleotide synthesis.

Example 4

Quenching Efficiency of Amino-Oxy Quencher Derivatives

This example demonstrates the signal to noise ratio (S:N) ratio of oligonucleotides containing both fluorescein and the azo quencher as prepared in Examples 1 through 3. Fluorescence-quenched probes are employed in a variety of applications in molecular biology. One method to assess if a given fluorophore and a quencher function well together is by measurement of a signal to noise ratio (S:N), where relative fluorescence is measured in the native configuration (background fluorescence or "noise") and compared with fluorescence measured when fluorophore and quencher are separated ("signal").

Oligonucleotide Synthesis. The following oligonucleotides were synthesized using standard phosphoramidite chemistry and the aminooxy quencher reagents described in Example 3, supra. Oligonucleotides were purified by HPLC. Dual-labeled oligonucleotides were made with the novel aminooxy (1-nitro-4-naphthylazo)-N,N-diethanolaniline quencher (6) of the invention at the 3'-end of the probe with the fluorescein reporter group placed at the 5' end (6-FAM, single isomer 6-carboxyfluorescein, Glen Research, Sterling, Va.). The same sequence was made using different methods of quencher attachment, including conjugation of the aminooxy quencher (6) post-synthetically (IBAOket), conjugation of the aminooxy quencher (6)-dU-CPG at the time of synthesis (IBAOdU, Formula V, supra), and conjugation of the aminooxy quencher (6)-ketone-CPG at the time of synthesis (IABAOC7, Formula (IV), supra). For comparison purposes, an oligonucleotide was made that incorporates a commercially available quenching group, Eclipse Quencher™-CPG (Epoch Biosciences, Bothell, Wash.). The Eclipse Quencher probe does not contain an aminooxy nucleophile. In order to make 3'- or internal FAM modification using ketone phosphoramidite (SEQ ID NO: 5), FAM-oxime conjugate has to be acetylated with acetic anhydride capping reagent prior following phosphoramidite cycle.

Electrospray-ionization liquid chromatography mass spectroscopy (ESI-LCMS) of each oligonucleotide probe was performed using an Oligo HTCS system (Novatia, Princeton, N.J.), which consisted of ThermoFinnigan TSQ7000, Xcalibur data system, ProMass data processing software and Paradigm MS4™ HPLC (Michrom BioResources, Auburn, Calif.). Protocols recommended by manufacturers were followed. Experimental molar masses for all compounds were within 0.02% of expected molar mass, confirming the identity of the compounds synthesized.

TABLE 2

| Probe | Sequence |
|---|---|
| SEQ ID NO: 1 | FAM-CCAGCGACCCTGATTATGGCCTCCCT-IBAOket |
| SEQ ID NO: 2 | FAM-CCAGCGACCCTGATTATGGCCTCCCT-IBAOdU |
| SEQ ID NO: 3 | FAM-CCAGCGACCCTGATTATGGCCTCCCT-IBAOC7 |
| SEQ ID NO: 4 | FAM-CCAGCGACCCTGATTATGGCCTCCCT-Eclipse |

As representative of the final structure obtained using reagents outlined in Example 3 in oligonucleotide synthesis, the chemical linkage between aminooxy quencher and the 3'-end of oligonucleotide SEQ ID NO: 3 is shown below (Formula (VII)).

TABLE 3

Signal to Noise ratios for Fluorescence-Quenched Linear Oligonucleotides.

| Probe ID | Dye/Quencher 5'-3' | RFU Background | RFU Signal | S:N Ratio |
|---|---|---|---|---|
| SEQ ID NO: 1 | FAM-IBAOket | 9.35E+05 | 7.25E+06 | 8 |
| SEQ ID NO: 2 | FAM-IBAOdU | 6.32E+05 | 9.13E+06 | 14 |
| SEQ ID NO: 3 | FAM-IBAOC7 | 4.85E+05 | 8.06E+06 | 17 |
| SEQ ID NO: 4 | FAM-Eclipse | 8.99E+05 | 1.19E+07 | 15 |

RFU = relative fluorescence units

As shown in Table 3, the novel aminooxy attached quenchers (6) are capable of quenching a fluorescein with similar efficiency as a commonly employed commercially available quencher group.

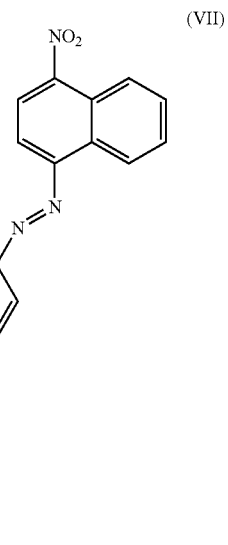
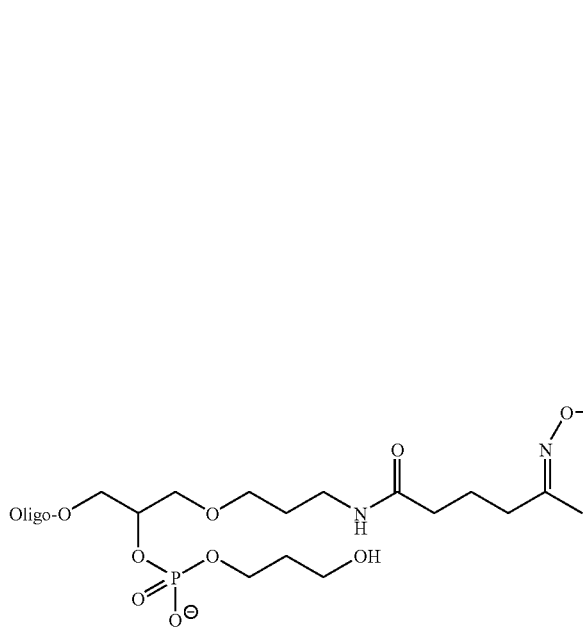

(VII)

Signal to Noise (S:N) Assay of Fluorescence-Quenched Linear Probes: Oligonucleotides were evaluated for quenching efficiency in a pre- and post-nuclease degradation assay. Probe oligonucleotides (SEQ ID NOS: 1-4) were individually resuspended at 100 nM concentration in HPLC-grade water. From this stock solution, 2 ml of 100 nM probe solution was prepared with STNR Buffer, comprising 10 mM Tris pH 8.3, 50 mM KCl, 5 mM $MgCl_2$, 1 mM $CaCl_2$, which was split into two identical 1 mL fractions. One fraction was retained without enzyme treatment as background control. The second fraction was subjected to nuclease degradation as follows. Micrococcal nuclease, 15 units (Roche, 15 U/ul), was added to the oligonucleotide solution and incubated at 37° C. for 1 hour. Relative fluorescence intensity for each sample was measured with a PTI QuantaMaster Model C-60 cuvette-based spectrofluorometer (Photon Technology International, Monmouth Jct., NJ). The fluorescence measurement of the solution containing intact probe constituted the "background" or "noise" component of the assay. The fluorescence measurement of the solution containing degraded probe (nuclease treated) constituted the "signal" component of the assay. Signal to noise ratios (S:N) were calculated.

Example 5

Use of Aminooxy-Quenchers in Fluorescent Probes in a Quantitative Real-Time PCR Assay Fluorescence-quenched probes can be employed to detect a target nucleic acid sequence. Commonly, such detection is linked to an amplification step, such as the polymerase chain reaction (PCR). This example demonstrates that use of fluorescent probes modified with aminooxy quenchers function in a relevant application, a real-time PCR assay.

Oligonucleotide primers were synthesized using standard phosphoramidite chemistry, desalted, and employed without additional purification. Probe oligonucleotides employed are the same compounds studied in Example 4 supra, SEQ ID NOS: 1-4. Primers employed are:

```
Forward Primer: HP48 For
AGAAGGTCATCATCTGCCATCG          SEQ ID NO: 5

Reverse Primer: HP48 Rev
TCCAGACTTTGGCTGTTCGGAT          SEQ ID NO: 6
```

The target nucleic acid is SEQ ID NO: 7, a 150 base pair (bp) amplicon derived from the human bHLH protein PTF1A gene (Genbank #NM_178161), cloned into the pCRII-TOPO vector (Invitrogen, Carlsbad, Calif.), and is hereafter referred to as the "p48-gene target".
Target Nucleic Acid Sequence:

SEQ ID NO: 7

HP48 For                                    HP48 Probe
AGAAGGTCATCATCTGCCATCGGGGCACCCGGTCCCCCTCCCCCAGCGACCCTGATTATGGCCTCCCTC

CCCTAGCAGGACACTCTCTCTCATGGACTGATGAAAAACAACTCAAGGAACAAAATATTATCCGAACA

GCCAAAGTCTGGA
      HP48 Rev

PCR amplification was done using the thermostable DNA polymerase Immolase™ (Bioline, Randolph, Mass.), 800 uM dNTPs, and 3 mM MgCl$_2$. Reactions were carried out in a 25 µL volume and comprised 200 nM each of the amplification primers and fluorescent quenched probe, 500, 50,000 and 5,000,000 copies of target DNA. Cycling conditions were 50° C. for 2 min, 95° C. for 10 min, then 40 cycles of 2-step PCR with 95° C. for 15 sec and 60° C. for 1 min. PCR and fluorescence measurements were done using an ABI Prism™ 7700 Sequence Detector (Applied Biosystems Inc., Foster City, Calif.). All data points were performed in triplicate. The cycle threshold (Ct) value is defined as the cycle at which a statistically significant increase in fluorescence is detected above background. A lower Ct value is indicative of a higher concentration of target DNA. The assays were performed using an identical amount of input target DNA ($5 \times 10^2$-$5 \times 10^4$-$5 \times 10^6$ copies of the PTF1a p48-gene target plasmid). Relative fluorescence levels collected during PCR for each probe were graphically plotted against cycle number and are shown in FIGS. 1-5.

Figure 6:
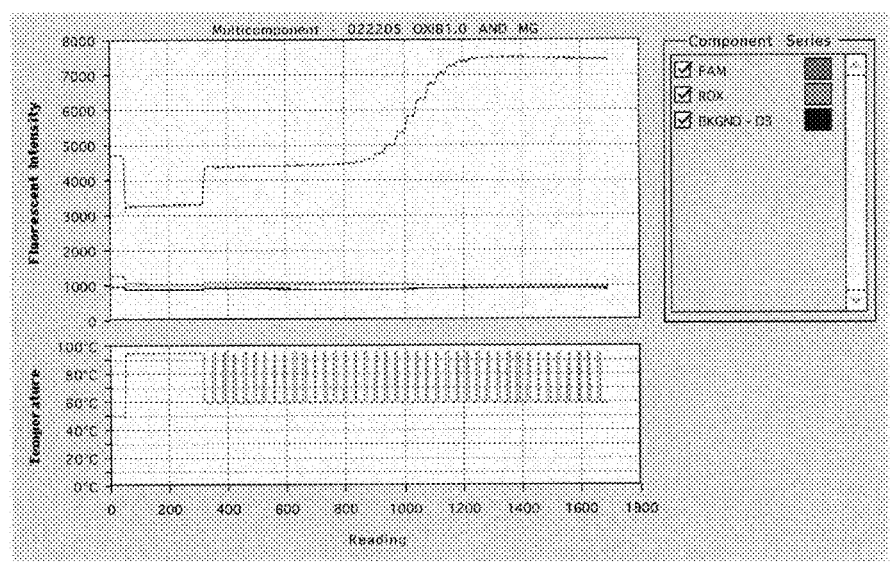
FIG. 6 shows real-time PCR data for Probe SEQ ID NO: 1 in a multicomponent view. Fluorescein data plot is positioned as the first curve in the upper graph and represents signal from the probe. Rox data plot is positioned as the second (flat) curve in the upper plot and represents detection control. Temperature trace during thermal cycling is plotted in the lower graph.

The multicomponent view of a 40-cycle real-time PCR reaction using probe SEQ ID NO: 1, which incorporates the aminooxy (1-nitro-4-naphthylazo)-N,N-diethanolaniline quencher (6) attached post-synthetically (IBAOket), is shown in FIG. 6. The fluorescence baseline remained flat until cycle 18, when product first reached detectable levels as a result of PCR amplification. The oxime bond was stable in the employed reaction conditions and no elevation of baseline background fluorescence was observed. The oxime bond is therefore suitable for use in these reaction conditions, which are similar to conditions commonly employed in many molecular biology applications.

Amplification traces for probe SEQ ID NO: 1, which incorporates the aminooxy (1-nitro-4-naphthylazo)-N,N-diethanolaniline quencher (6) attached post-synthetically (IBAOket), are shown in FIG. 6. The results showed good clustering of triplicate reactions and clearly distinguished between different input concentrations of the target nucleic acid.

Figure 7:
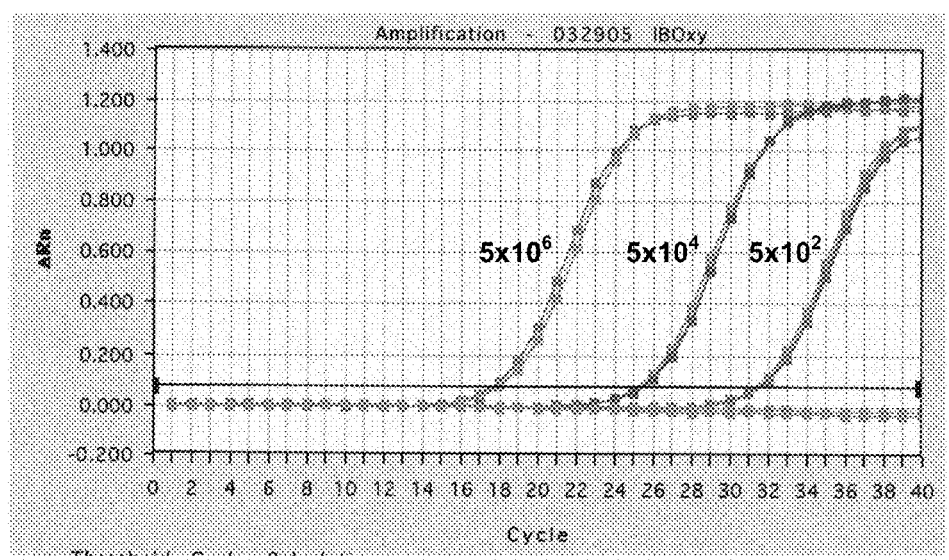
FIG. 7 shows real-time PCR data for Probe SEQ ID NO: 1 as amplification traces. Reactions were done using input target amounts of $5\times10^6$ molecules, $5\times10^4$ molecules, and $5\times10^2$ molecules which are shown left to right. All target concentrations were run in triplicate.

Amplification traces for probe SEQ ID NO: 2, which incorporates the aminooxy (1-nitro-4-naphthylazo)-N,N-diethanolaniline quencher (6) attached during synthesis as a CPG conjugate via a dU base linkage (IBAOdU), is shown in FIG. 7. The results showed good clustering of triplicate reactions and clearly distinguished between different input concentrations of the target nucleic acid.

Figure 8:
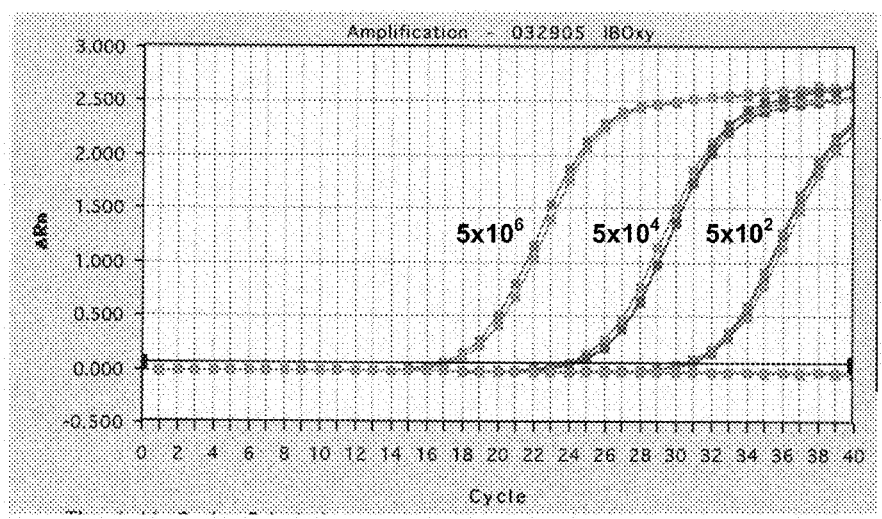
FIG. 8 shows real-time PCR amplification traces for Probe SEQ ID NO: 2. Reactions were done using input target amounts of $5\times10^6$ molecules, $5\times10^4$ molecules, and $5\times10^2$ molecules which are shown left to right. All target concentrations were run in triplicate.

Amplification traces for probe SEQ ID NO: 3, which incorporates the aminooxy (1-nitro-4-naphthylazo)-N,N-diethanolaniline quencher attached during synthesis as a CPG conjugate via direct linkage to the 3'-end of the oligonucleotide (IBAOC7), are shown in FIG. 8. The results showed good clustering of triplicate reactions and clearly distinguished between different input concentrations of the target nucleic acid.

Figure 9:
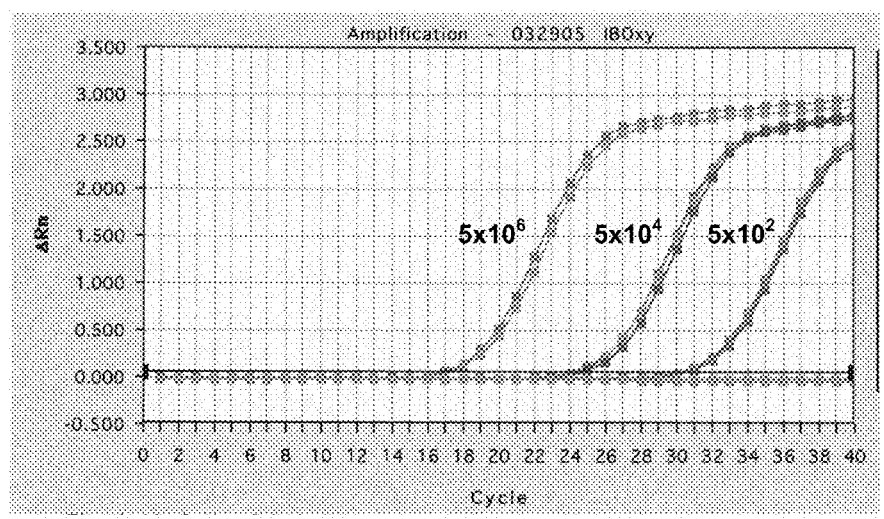
FIG. 9 shows real-time PCR amplification traces for Probe SEQ ID NO: 3. Reactions were done using input target amounts of $5\times10^6$ molecules, $5\times10^4$ molecules, and $5\times10^2$ molecules which are shown left to right. All target concentrations were run in triplicate.

Amplification traces for probe SEQ ID NO: 4, which incorporates commercial Eclipse Quencher attached during synthesis as a CPG conjugate via direct linkage to the 3'-end of the oligonucleotide (Eclipse), are shown in FIG. 9. The results showed good clustering of triplicate reactions and clearly distinguished between different input concentrations of the target nucleic acid.

Figure 10:
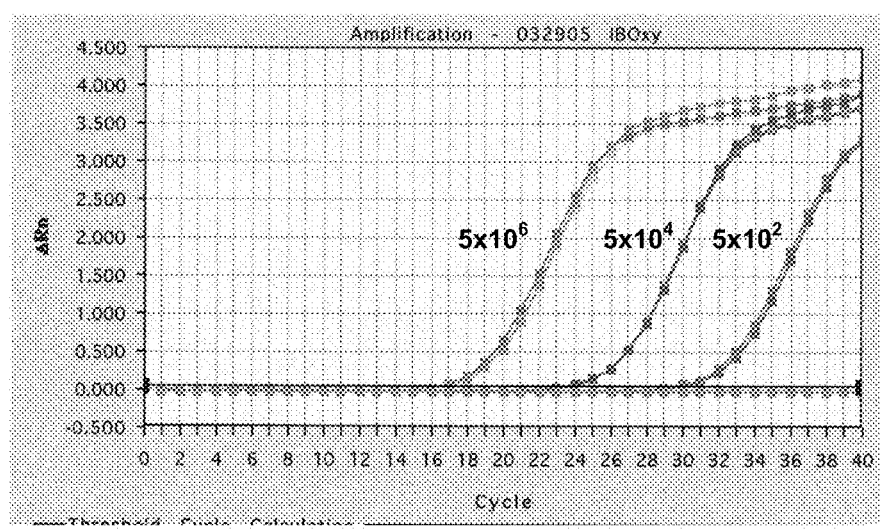
FIG. 10 shows real-time PCR amplification traces for Probe SEQ ID NO: 4. Reactions were done using input target amounts of $5\times10^6$ molecules, $5\times10^4$ molecules, and $5\times10^2$ molecules which are shown left to right. All target concentrations were run in triplicate.
Figure 11:
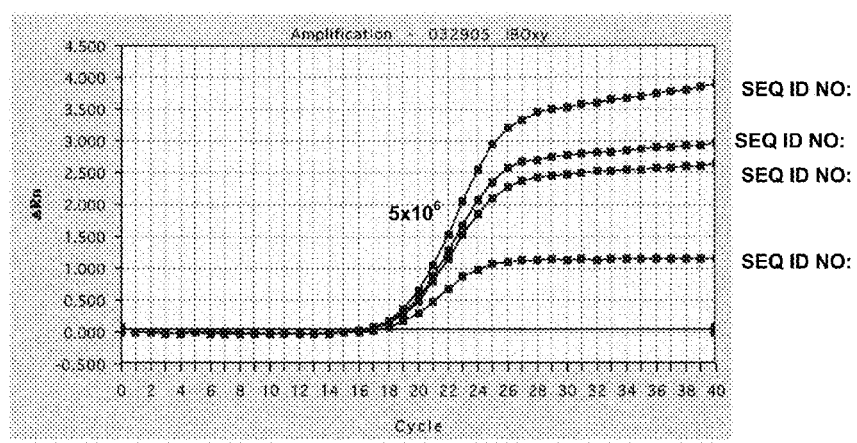
FIG. 11 shows real-time PCR amplification traces for Probe SEQ ID NOS: 1-4. Traces for each probe using $5\times10^6$ input target molecules are shown. All target concentrations were run in triplicate.

The real-time PCR results for all 4 probes were plotted together for a single target concentration, $5 \times 10^6$ and are shown in FIG. 10. The absolute change in fluorescence ($\Delta$Rf) varied between probes. This typically results from variable quality of purification at the time of synthesis. Actual sensitivity to quantitative detection of the input target nucleic acid was nearly identical between probes and quenchers employed.

Table 4 summarizes the real-time PCR results and demonstrates that all oligonucleotides provided similar Ct values regardless of method of quencher attachment and functioned with similar performance in this application.

TABLE 4

Relative Ct Values for Probes SEQ ID NOS: 1-4 in Real Time PCR Assay.

| Probe | Ave. Ct Target $5 \times 10^6$ | Ave. Ct Target $5 \times 10^4$ | Ave. Ct Target $5 \times 10^2$ |
|---|---|---|---|
| SEQ ID NO: 1 | 17.9 | 25.3 | 31.4 |
| SEQ ID NO: 2 | 17.1 | 24.5 | 30.5 |
| SEQ ID NO: 3 | 17.2 | 24.3 | 30.8 |
| SEQ ID NO: 4 | 16.9 | 24.0 | 30.1 |

As shown in Table 4, probe compositions comprising the new aminooxy (1-nitro-4-naphthylazo)-N,N-diethanolaniline quencher (6) of the invention performed well in a quantitative real-time PCR assay and were functionally interchangeable with probes that contain other quencher moieties.

Example 6

Use of Internal Aminooxy-Du Quenchers in Fluorescent Probes Function in a Quantitative Real-Time PCR Assay Quencher groups are commonly placed at the end of a probe sequence for ease of synthesis. The new aminooxy quencher permits internal incorporation of quencher as a base modified aminooxy quencher-dU moiety. This example demonstrates that use of fluorescent probes modified with internal aminooxy-quenchers function better in a real-time PCR assay than standard end-quenched probes.

Dual-labeled oligonucleotides with internal modifications (SEQ ID NOS: 12-14) were made using ketone-dU phosphoramidite (synthesized according to published procedure: Dey & Shepard, (2001) Org. Lett., v. 3, pp. 3983-3986, which is incorporated by reference herein) followed by interconjugation with 300 µL of 10 mM solution (per 1 µmole of the oligonucleotide on the solid support) of the aminooxy-quencher reagent (6) in ethanol at the time of synthesis. After 2 hours, excess aminooxy-quencher was removed, the solid support was washed with 1 mL of acetonitrile and the oligonucleotide was extended using standard phosphoramidite chemistry.

Oligonucleotide primers were synthesized using standard phosphoramidite chemistry, desalted, and were used in the assay without additional purification. Primer and probe oligonucleotides employed are shown below. Probes with internal quencher modifications had a C3 spacer group placed at the 3'-end in place of the quencher group to block extension during PCR. Oligonucleotides were synthesized as described above.

TABLE 5

| Sequence | SEQ ID NO: |
|---|---|
| 5' FAM-ATGGCGGTTCTCATGCTGGCAAC-IBAOC7 3' | SEQ ID NO: 11 |
| 5' FAM-ATGGCGGT(iIBAOdU)CTCATGCTGGCAAC-C3sp 3' | SEQ ID NO: 12 |
| 5' FAM-ATGGCGGTT(iIBAOdU)TCATGCTGGCAAC-C3sp 3' | SEQ ID NO: 13 |
| 5' FAM-ATGGCGGTTCTC(iIBAOdU)TGCTGGCAAC-C3sp 3' | SEQ ID NO: 14 |
| 5' AACTCTGAAGTCATCCTGCCAGTC 3' | SEQ ID NO: 8 |
| 5' CTTCAGGTTGTGGTAAACCTCTGC 3' | SEQ ID NO: 9 |

The forward and reverse primers are shown in SEQ ID NOS: 8 and 9. Internal aminooxy-quencher-dU is notated by (iIBAOdU). SEQ ID NO: 11 represents a traditional probe with 3'-terminal quencher placement. SEQ ID NO: 12 has an internal aminooxy-quencher-dU substitution for an internal dT base at position 9 from the 5'-end. SEQ ID NO: 13 has an internal aminooxy-quencher-dU substitution for an internal dC base at position 10 from the 5'-end, which results in a favorable U:G base pairing event upon hybridization. SEQ ID NO: 14 has an internal aminooxy-quencher-dU substitution for an internal dA base at position 13 from the 5'-end, which results in an unfavorable U:T base pairing event upon hybridization. The aminooxy-quencher-dU base is compound (20a_.

The target nucleic acid is SEQ ID NO: 10, a 162 base pair (bp) amplicon derived from the human Enolase gene (Genbank #NM_001428), cloned into the pCRII-TOPO vector (Invitrogen, Carlsbad, Calif.), and is hereafter referred to as the "hEnolase-gene target".

Figure 12:
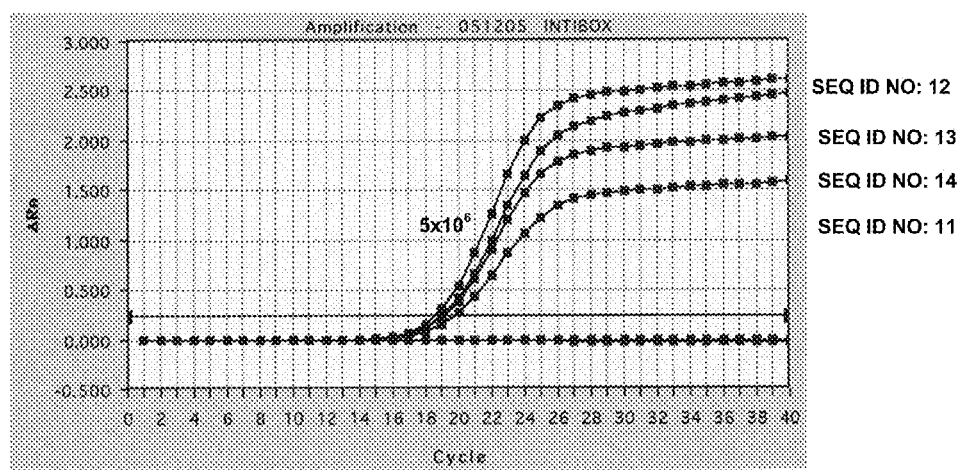
FIG. 12 shows real-time PCR amplification traces for probe SEQ ID NOS: 11-14. Traces for each probe using $5\times10^6$ input target molecules are shown. All target concentrations were run in triplicate.

Target Nucleic Acid Sequence:

PCR amplification was performed using the thermostable DNA polymerase Immolase™ (Bioline, Randolph, Mass.), 800 uM dNTPs, and 3 mM $MgCl_2$. Reactions were carried out in a 25 µL, volume and comprised 200 nM each of the amplification primers and fluorescent quenched probe, 500, 50,000 and 5,000,000 copies of target DNA. Cycling conditions were 50° C. for 2 min, 95° C. for 10 min, then 40 cycles of 2-step PCR with 95° C. for 15 sec and 65° C. for 1 min. PCR and fluorescence measurements were done using an ABI Prism™ 7700 Sequence Detector (Applied Biosystems Inc., Foster City, Calif.). All data points were performed in triplicate. The cycle threshold (Ct) value is defined as the cycle at which a statistically significant increase in fluorescence is detected above background. A lower Ct value is indicative of a higher concentration of target DNA. The assays were performed using an identical amount of input target DNA ($5 \times 10^2$-$5 \times 10^4$-$5 \times 10^6$ copies of the hEnolase-gene target plasmid). Relative fluorescence levels collected during PCR for each probe were graphically plotted against cycle number. The real-time PCR results for all 4 probes are plotted together for a single target concentration, $5 \times 10^6$ and are shown in FIG. 12. The absolute change in fluorescence (ΔRf) varied noticeably between probes. In this case, probes had similar quality and the differences in fluorescence relates to different potency of quenching that varies with quencher placement. Actual sensitivity to quantitative detection of the input target nucleic acid varied between probes and is quantified in Table 6 below.

TABLE 6

| | Relative Ct Values for Probes SEQ ID NOS: 10-13 in Real Time PCR Assay. | | |
|---|---|---|---|
| Probe | Ave. Ct Target $5 \times 10^6$ | Ave. Ct Target $5 \times 10^4$ | Ave. Ct Target $5 \times 10^2$ |
| SEQ ID NO: 11 | 19.8 | 26.5 | 33.3 |
| SEQ ID NO: 12 | 18.6 | 25.4 | 32.2 |
| SEQ ID NO: 13 | 19.1 | 25.8 | 32.6 |
| SEQ ID NO: 14 | 19.1 | 25.7 | 32.6 |

SEQ ID NO: 10

Enolase For                           Enolase Probe
<u>AACTCTGAAGTCATCCTGCCAGTC</u>CCCGGCGTTCAATGTCATC<u>AATGGCGGTTCTCATGCTGGCAAC</u>AAGCTGGCCAT GCAGGAGTTCATGATCCTCCCAGTCGGTGCAGCAAACTTCAGGGAAGCCATGCGCATTGG<u>AGCAGAGGTTTACCACA</u>

<u>ACCTGAAG</u>
    Enolase Rev

Probe compositions comprising the new aminooxy (1-nitro-4-naphthylazo)-N,N-diethanolaniline quencher (6) placed internally on a dU base show superior properties in a real-time PCR assay compared with standard 3'-quencher probes. Detection limits were improved by ~1 Ct value, which corresponds to about double detection sensitivity.

Example 7

Absorbance Spectrum

This example shows an absorbance spectrum of an oligonucleotide modified at its 5'terminus to contain the azo-quencher (6). The oligonucleotide was made using standard automated phosphoramidite nucleotide synthetic methods where the last addition cycle was carried out with the molecule (6). The composition of the oligonucleotide is shown below.

SEQ ID NO: 15    (Azo-Quencher)-CAGAGTACCTGA

Once synthesized, the oligonucleotide was suspended in HPLC-grade water at 400 nM concentration. Optical absorbance was measured in 10 mM Tris pH 8.0, 1 mM EDTA (TE buffer) with a sub-micro quartz cuvette with 1-cm path length in a Hewlett Packard Model 8453 spectrophotometer (Hewlett Packard, Palo Alto, Calif.). Absorbance density was recorded from 220 nm to 700 nm and is shown in FIG. 13.

Figure 13:
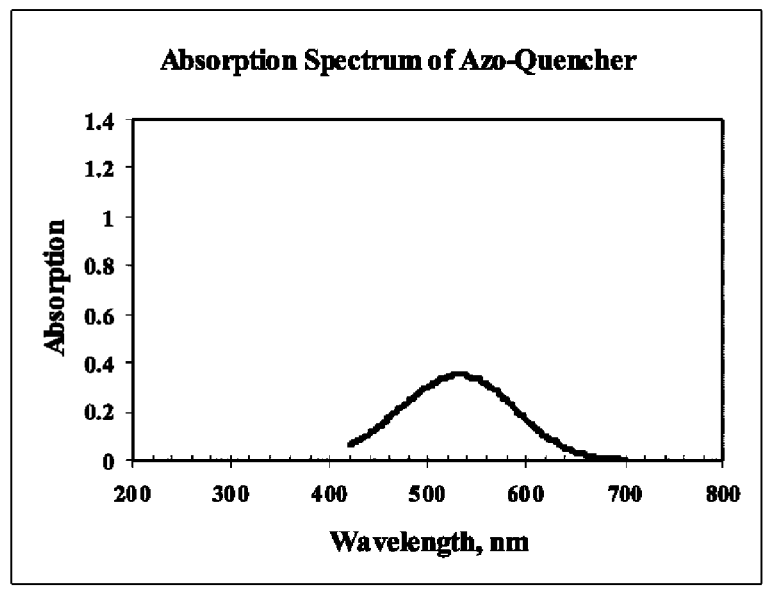
FIG. 13 shows the absorbance spectrum of an oligonucleotide of SEQ ID NO: 15.

As shown in FIG. 13, the absorbance spectrum was broad, ranging from 420 to 620 nm, with peak absorbance at 531 nm. This absorbance range overlaps with the fluorescence emission of a wide variety of fluorophores commonly used in molecular biology applications. For FRET based quenching mechanisms, this spectrum is positioned to offer maximum quenching capacity for dyes in the spectral range of fluorescein.

Example 8

The aminooxy group is introduced to a reporter moiety via the Mitsunobu reaction between alcohol (21) and N-hydroxyphthalimide followed by phthalimide hydrolysis. (Scheme 4 in FIG. 4).

This method can be used for derivatization of fluorophores, quenchers, biotin, peptides and other reporter moieties stable to basic conditions.

Example 9

In case of base labile molecules, such as some peptides, proteins, reporter moieties having alkylamino function, the aminooxy group is introduced by reaction with corresponding NHS ester (28), followed by removal of acid liable MMT group. (Scheme 5 in FIG. 5).

Example 10

Synthesis of Fluorescein Aminooxy Derivative (33)

This example demonstrates the chemical synthesis of the compound of formula:

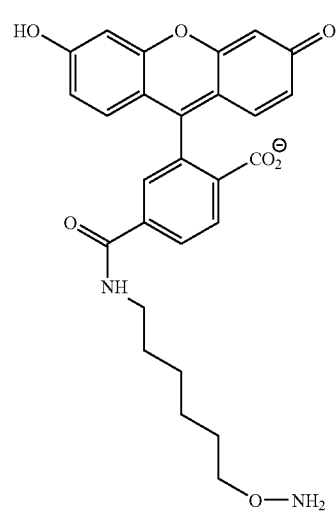

Figure 14:
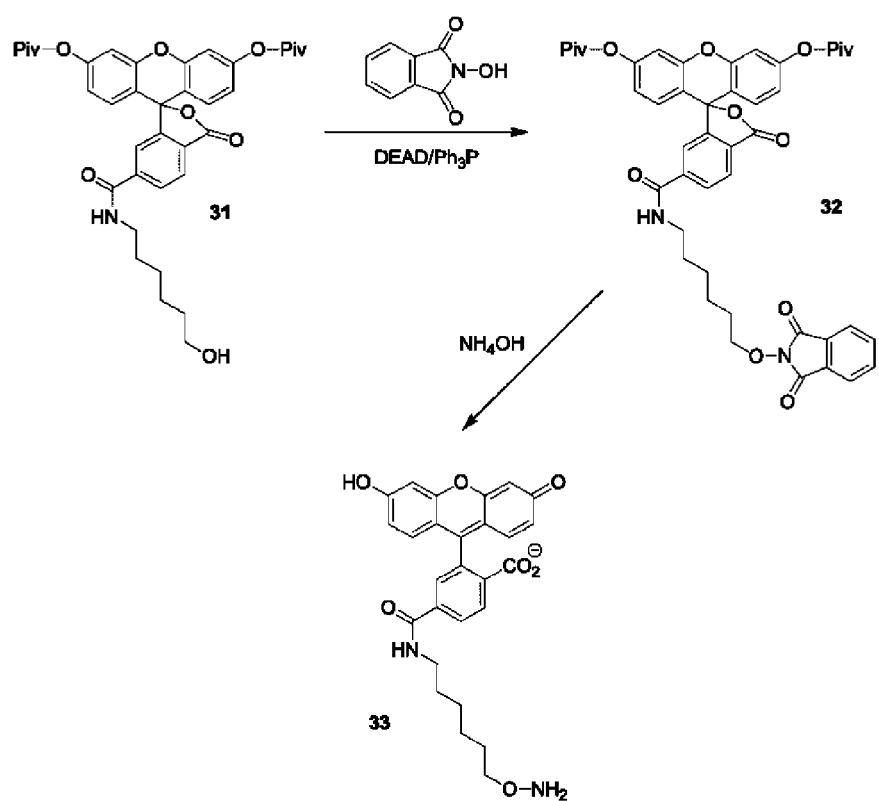
FIG. 14 shows the synthesis of a fluorescein aminooxy derivative.

The synthesis was as shown in FIG. 14 below. To the solution of 0.72 g (0.14 mmol) alcohol (31), 0.23 g (0.14 mmol) N-hydroxy-phthalimide, and 0.36 g (0.14 mmol) of triphenylphosphine in 10 mL of THF was added 0.26 mL (0.15 mmol) of DEAD. After overnight stirring the reaction mixture was concentrated under diminished pressure. Flash chromatography with 1:4 EtOAc/hexanes provided 380 mg of (32). TLC: $R_f$ 0.55 (EtOAc/hexanes—60/40). $^1$H NMR (CDCl$_3$) δ 8.13 (d, J=8.4 Hz, 1H), 8.07 (d, J=8.4 Hz, 1H), 7.7-7.9 (m, 4H), 7.49 (s, 1H), 7.03 (d, 2.4 Hz, 2H), 6.75-6.83 (m, 4H), 6.42 (t, J=6.5 Hz, 1H), 4.21 (t, J=6.5 Hz, 2H) 3.45 (dd, J=8.5, J=6.5, 2H), 1.35-1.80 (m, 8H), 1.36 (s, 18H).

The solution of 10 mg (32) in 2 mL of concentrated ammonia solution in ethanol was incubated overnight at 55° C. The solvent was removed under diminished pressure to provide (33) that was used further without purification.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Variations of those preferred embodiments may become apparent to those of ordinary skill in the art upon reading the foregoing description. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound comprising Formula (I):

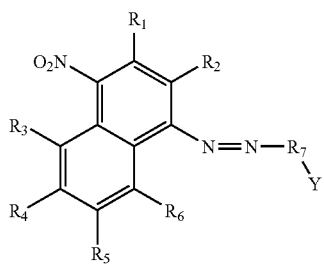

(I)

wherein $R_{1-6}$ are independently selected from the group consisting of an electron withdrawing group, an alkyl group, an aryl group, hydrogen, a heteroaryl group, and a five or six member ring structure formed from the $R_1$ and $R_2$ pair, the $R_3$ and $R_4$ pair, the $R_4$ and $R_5$ pair, or the $R_5$ and $R_6$ pair;

$R_7$ is a substituted or unsubstituted aryl group; and

Y is an oxime forming nucleophile.

2. The compound of claim 1, wherein the oxime forming nucleophile is aminooxy.

3. The compound of claim 1, wherein the oxime forming nucleophile is hydrazine.

4. The compound of claim 1, wherein the electron withdrawing group is independently selected from the group consisting of halogen, $NO_2$, $SO_3R_S$, $SO_2N(R_N)_2$, CN, CNS, keto, and alkoxy groups; wherein $R_N$ and $R_S$ are independently selected from the group consisting of $C_1$-$C_{10}$ alkyl groups, which are branched or unbranched, saturated or unsaturated, and substituted or unsubstituted, and aryl groups, which are substituted or unsubstituted.

5. The compound of claim 1, wherein at least one of $R_{1-6}$ is an electron withdrawing group.

6. The compound of claim 1, wherein at least one of $R_{1-6}$ is an alkyl group.

7. The compound of claim 6, wherein the alkyl group has from one to ten carbon atoms.

8. The compound of claim 1, wherein at least one of $R_{1-6}$ is an aryl group.

9. The compound of claim 1, wherein at least one of $R_{1-6}$ is a heteroaryl group.

10. The compound of claim 1, wherein at least one of $R_{1-6}$ is a hydrogen.

11. The compound of claim 1, wherein at least one of the $R_1$ and $R_2$ pair, the $R_3$ and $R_4$ pair, the $R_4$ and $R_5$ pair, or the $R_5$ and $R_6$ pair are combined to form a ring having five or six ring members.

12. The compound of claim 11, wherein the ring has six ring members.

13. The compound of claim 1, wherein $R_7$ is an aryl group.

14. The compound of claim 13, wherein the aryl group is selected from the group consisting of phenyl, naphthyl, xylyl, tolyl, pyridyl, and anilinyl.

15. The compound of claim 14, wherein the aryl group is an anilinyl group.

16. The compound of claim 15, wherein the anilinyl group comprises:

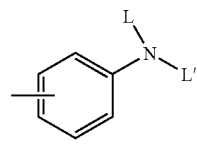

(III)

wherein L and L' are independently selected from the group consisting of substituted or unsubstituted $C_{1-10}$ alkyl, wherein the $C_{1-10}$ alkyl groups are saturated or unsaturated; and wherein one of L or L' is substituted with an oxime forming nucleophile substituent.

17. A compound comprising:

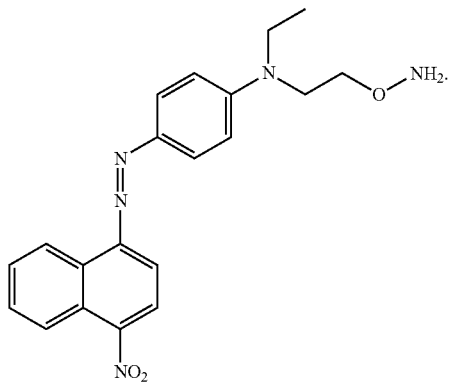

18. A compound comprising:

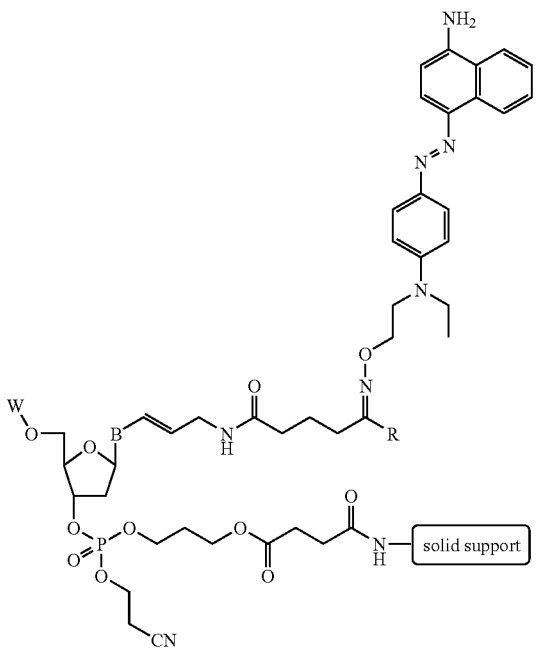

wherein R is an alkyl group, B is a nucleobase, and W is selected from the group consisting of a protecting group, an oligonucleotide, a nucleotide or a nucleoside.

19. The composition of claim 18, wherein the nucleobase is selected from the group consisting of adenine, guanine, cytosine, uracil and thymine.

20. The composition of claim 19, wherein the nucleobase is uracil.

21. A compound comprising Formula (I):

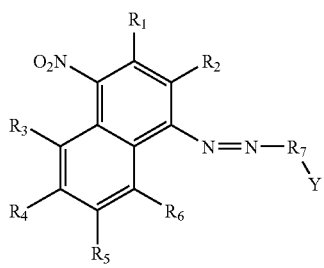

wherein $R_{1-6}$ are independently selected from the group consisting of an electron withdrawing group, an alkyl group, an aryl group, hydrogen, a heteroaryl group, and a five or six member ring structure formed from the $R_1$ and $R_2$ pair, the $R_3$ and $R_4$ pair, the $R_4$ and $R_5$ pair, or the $R_5$ and $R_6$ pair, and wherein at least one of $R_{1-6}$ is an alkyl group, an aryl group or a heteroaryl group;

$R_7$ is a substituted or unsubstituted aryl group; and

Y is a nucleophile.

22. A compound comprising Formula (I):

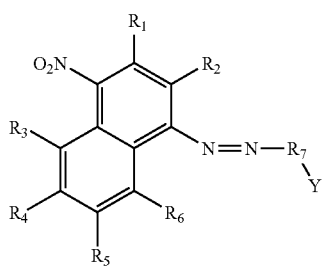

wherein $R_{1-6}$ are independently selected from the group consisting of an electron withdrawing group, an alkyl group, an aryl group, hydrogen, a heteroaryl group, and a five or six member ring structure formed from the $R_1$ and $R_2$ pair, the $R_3$ and $R_4$ pair, the $R_4$ and $R_5$ pair, or the $R_5$ and $R_6$ pair, and wherein at least one of the $R_1$ and $R_2$ pair, the $R_3$ and $R_4$ pair, the $R_4$ and $R_5$ pair, or the $R_5$ and $R_6$ pair are combined to form a ring having five or six ring members;

$R_7$ is a substituted or unsubstituted aryl group; and

Y is a nucleophile.

23. The compound of claim 22, wherein the ring has six ring members.

24. A compound comprising Formula (I):

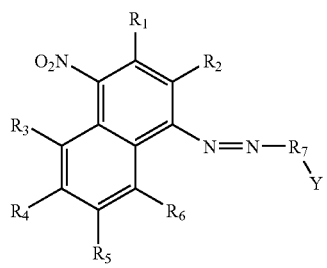

wherein $R_{1-6}$ are independently selected from the group consisting of an electron withdrawing group, an alkyl group, an aryl group, hydrogen, a heteroaryl group, and a five or six member ring structure formed from the $R_1$ and $R_2$ pair, the $R_3$ and $R_4$ pair, the $R_4$ and $R_5$ pair, or the $R_5$ and $R_6$ pair;

$R_7$ is an anilinyl group; and

Y is a nucleophile.

25. The compound of claim 24, wherein the anilinyl group comprises:

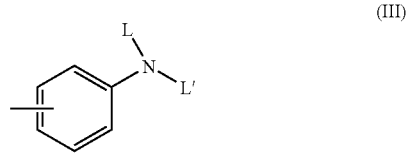

wherein L and L' are independently selected from the group consisting of substituted or unsubstituted $C_{1-10}$ alkyl, wherein the $C_{1-10}$ alkyl groups are saturated or unsaturated; and wherein one of L or L' is substituted with an oxime forming nucleophile substituent.

* * * * *

```
                        SEQUENCE LISTING

<160> NUMBER OF SEQ ID NOS: 15

<210> SEQ ID NO 1
<211> LENGTH: 26
<212> TYPE: DNA
<213> ORGANISM: Artificial
<220> FEATURE:
<223> OTHER INFORMATION: Synthetic oligonucleotide

<400> SEQUENCE: 1
ccagcgaccc tgattatggc ctccct                                              26

<210> SEQ ID NO 2
<211> LENGTH: 27
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (27)..(27)
<223> OTHER INFORMATION: IBAOdU Iowa Black deoxyuracil
<220> FEATURE:
<221> NAME/KEY: misc_feature
<222> LOCATION: (27)..(27)
<223> OTHER INFORMATION: n is a, c, g, or t

<400> SEQUENCE: 2
ccagcgaccc tgattatggc ctccctn                                             27

<210> SEQ ID NO 3
<211> LENGTH: 26
<212> TYPE: DNA
<213> ORGANISM: Artificial
<220> FEATURE:
<223> OTHER INFORMATION: Synthetic oligonucleotide

<400> SEQUENCE: 3
ccagcgaccc tgattatggc ctccct                                              26

<210> SEQ ID NO 4
<211> LENGTH: 26
<212> TYPE: DNA
<213> ORGANISM: Artificial
<220> FEATURE:
<223> OTHER INFORMATION: Synthetic oligonucleotide

<400> SEQUENCE: 4
ccagcgaccc tgattatggc ctccct                                              26

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide

<400> SEQUENCE: 5
```

```
agaaggtcat catctgccat cg                                            22

<210> SEQ ID NO 6
<211> LENGTH: 22
<212> TYPE: DNA
<213> ORGANISM: Artificial
<220> FEATURE:
<223> OTHER INFORMATION: Synthetic oligonucleotide

<400> SEQUENCE: 6
tccagacttt ggctgttcgg at                                            22

<210> SEQ ID NO 7
<211> LENGTH: 150
<212> TYPE: DNA
<213> ORGANISM: Artificial
<220> FEATURE:
<223> OTHER INFORMATION: Synthetic oligonucleotide

<400> SEQUENCE: 7
agaaggtcat catctgccat cggggcaccc ggtcccccctc ccccagcgac cctgattatg   60
gcctccctcc cctagcagga cactctctct catggactga tgaaaaacaa ctcaaggaac  120
aaaatattat ccgaacagcc aaagtctgga                                    150

<210> SEQ ID NO 8
<211> LENGTH: 24
<212> TYPE: DNA
<213> ORGANISM: Artificial
<220> FEATURE:
<223> OTHER INFORMATION: Synthetic oligonucleotide

<400> SEQUENCE: 8
aactctgaag tcatcctgcc agtc                                          24

<210> SEQ ID NO 9
<211> LENGTH: 24
<212> TYPE: DNA
<213> ORGANISM: Artificial
<220> FEATURE:
<223> OTHER INFORMATION: Synthetic oligonucleotide

<400> SEQUENCE: 9
cttcaggttg tggtaaacct ctgc                                          24

<210> SEQ ID NO 10
<211> LENGTH: 162
<212> TYPE: DNA
<213> ORGANISM: Artificial
<220> FEATURE:
<223> OTHER INFORMATION: Synthetic oligonucleotide

<400> SEQUENCE: 10
aactctgaag tcatcctgcc agtcccggcg ttcaatgtca tcaatggcgg ttctcatgct   60
ggcaacaagc tggccatgca ggagttcatg atcctcccag tcggtgcagc aaacttcagg  120
gaagccatgc gcattggagc agaggtttac cacaacctga ag                     162

<210> SEQ ID NO 11
<211> LENGTH: 23
<212> TYPE: DNA
<213> ORGANISM: Artificial
<220> FEATURE:
<223> OTHER INFORMATION: Synthetic oligonucleotide

<400> SEQUENCE: 11
```

```
atggcggttc tcatgctggc aac                                              23

<210> SEQ ID NO 12
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (9)..(9)
<223> OTHER INFORMATION: IBAOdU Iowa Black deoxyuracil
<220> FEATURE:
<221> NAME/KEY: misc_feature
<222> LOCATION: (9)..(9)
<223> OTHER INFORMATION: n is a, c, g, or t

<400> SEQUENCE: 12 atgcggtnc tcatgctggc aac                                               23

<210> SEQ ID NO 13
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (10)..(10)
<223> OTHER INFORMATION: IBAOdU Iowa Black deoxyuracil
<220> FEATURE:
<221> NAME/KEY: misc_feature
<222> LOCATION: (10)..(10)
<223> OTHER INFORMATION: n is a, c, g, or t

<400> SEQUENCE: 13 atgcggttn tcatgctggc aac                                               23

<210> SEQ ID NO 14
<211> LENGTH: 23
<212> TYPE: DNA
<213> ORGANISM: Artificial
<220> FEATURE:
<223> OTHER INFORMATION: Synthetic oligonucleotide
<220> FEATURE:
<221> NAME/KEY: modified_base
<222> LOCATION: (13)..(13)
<223> OTHER INFORMATION: IBAOdU Iowa Black deoxyuracil
<220> FEATURE:
<221> NAME/KEY: misc_feature
<222> LOCATION: (13)..(13)
<223> OTHER INFORMATION: n is a, c, g, or t

<400> SEQUENCE: 14 atgcggttc tcntgctggc aac                                               23

<210> SEQ ID NO 15
<211> LENGTH: 12
<212> TYPE: DNA
<213> ORGANISM: Artificial
<220> FEATURE:
<223> OTHER INFORMATION: Synthetic oligonucleotide

<400> SEQUENCE: 15
cagagtacct ga                                                          12
```